US010028716B2

(12) United States Patent
Rössl

(10) Patent No.: US 10,028,716 B2
(45) Date of Patent: Jul. 24, 2018

(54) DIFFERENTIAL PHASE-CONTRAST IMAGING

(75) Inventor: Ewald Rössl, Ellerau (DE)

(73) Assignee: KONIKLIJKE PHILIPS N.V., Eindhoven (NL)

(*) Notice: Subject to any disclaimer, the term of this patent is extended or adjusted under 35 U.S.C. 154(b) by 813 days.

(21) Appl. No.: 13/878,767

(22) PCT Filed: Oct. 12, 2011

(86) PCT No.: PCT/IB2011/054500
§ 371 (c)(1),
(2), (4) Date: Apr. 11, 2013

(87) PCT Pub. No.: WO2012/052881
PCT Pub. Date: Apr. 26, 2012

(65) Prior Publication Data
US 2013/0208864 A1 Aug. 15, 2013

(30) Foreign Application Priority Data
Oct. 19, 2010 (EP) .................... 10187976

(51) Int. Cl.
*A61B 6/00* (2006.01)
*G21K 1/06* (2006.01)
(Continued)

(52) U.S. Cl.
CPC ............ *A61B 6/484* (2013.01); *A61B 6/4291* (2013.01); *G01N 23/04* (2013.01); *G01T 7/00* (2013.01);
(Continued)

(58) Field of Classification Search
CPC ........ A61B 6/4291; A61B 6/484; G21K 1/06; G21K 1/067
(Continued)

(56) References Cited

U.S. PATENT DOCUMENTS 5,812,629 A * 9/1998 Clauser .......................... 378/62
6,968,041 B2 * 11/2005 Hoheisel et al. ............. 378/154
(Continued)

FOREIGN PATENT DOCUMENTS

EP     1731099       12/2006
JP     2012045099 A  3/2012
(Continued)

OTHER PUBLICATIONS

"Phase-Contrast X-Ray Imaging", From Wikipedia, the Free Encyclopedia, Downloaded Apr. 12, 2015, pp. 1-25.
(Continued)

*Primary Examiner* — Allen C. Ho
(74) *Attorney, Agent, or Firm* — Larry Liberchuk

(57) ABSTRACT

The present invention relates to differential phase-contrast imaging, in particular to a structure of a diffraction grating, e.g. an analyzer grating and a phase grating, for X-ray differential phase-contrast imaging. In order to make better use of the X-ray radiation passing the object, a diffraction grating (14) for X-ray differential phase-contrast imaging is provided with at least one portion (24) of a first sub-area (26) and at least one portion (28) of a second sub-area (30). The first sub-area comprises a grating structure (54) with a plurality of bars (34) and gaps (36) being arranged periodically with a first grating pitch P G (38), wherein the bars are arranged such that thy change the phase and/or amplitude of an X-ray radiation and wherein the gaps are X-ray transparent. The second sub-area is X-ray transparent and wherein the at least one portion of the second sub-area provides an X-ray 1 transparent aperture (40) in the grating. Portions of the first and second sub-areas are arranged in an alternating manner in at least one direction (42).

28 Claims, 18 Drawing Sheets

(51) Int. Cl.
*G01N 23/04* (2018.01)
*G01T 7/00* (2006.01)

(52) U.S. Cl.
CPC .............. *G21K 1/06* (2013.01); *G21K 1/067* (2013.01); *A61B 6/4092* (2013.01); *A61B 6/4441* (2013.01); *G01N 2223/064* (2013.01); *G01N 2223/1016* (2013.01); *G01N 2223/612* (2013.01)

(58) Field of Classification Search
USPC .............. 378/19, 36, 62, 147, 149, 154, 155
See application file for complete search history.

(56) References Cited

U.S. PATENT DOCUMENTS

| | | | |
|---|---|---|---|
| 7,180,979 B2* | 2/2007 | Momose | 378/62 |
| 7,433,444 B2* | 10/2008 | Baumann et al. | 378/62 |
| 7,486,770 B2* | 2/2009 | Baumann | A61B 6/032 378/145 |
| 7,492,871 B2* | 2/2009 | Popescu et al. | 378/145 |
| 7,522,698 B2* | 4/2009 | Popescu | A61B 6/032 378/19 |
| 7,522,708 B2* | 4/2009 | Heismann et al. | 378/145 |
| 7,535,986 B2* | 5/2009 | Hempel | A61B 5/02007 378/4 |
| 7,564,941 B2* | 7/2009 | Baumann et al. | 378/19 |
| 7,639,786 B2* | 12/2009 | Baumann et al. | 378/145 |
| 7,646,843 B2* | 1/2010 | Popescu et al. | 378/5 |
| 7,746,981 B2* | 6/2010 | Takahashi et al. | 378/98.8 |
| 7,869,567 B2* | 1/2011 | Olivo | G01N 23/04 378/62 |
| 7,889,838 B2* | 2/2011 | David et al. | 378/36 |
| 7,924,973 B2* | 4/2011 | Kottler | G01B 15/025 378/36 |
| 7,945,018 B2* | 5/2011 | Heismann | A61B 6/032 378/145 |
| 7,949,095 B2* | 5/2011 | Ning et al. | 378/62 |
| 7,983,381 B2* | 7/2011 | David | A61B 6/032 378/4 |
| 8,005,185 B2* | 8/2011 | Popescu | 378/36 |
| 8,009,796 B2* | 8/2011 | Popescu | A61B 6/032 378/19 |
| 8,009,797 B2* | 8/2011 | Ouchi | G01N 23/04 378/36 |
| 8,041,004 B2* | 10/2011 | David et al. | 378/36 |
| 8,139,711 B2* | 3/2012 | Takahashi | 378/62 |
| 8,184,771 B2* | 5/2012 | Murakoshi et al. | 378/62 |
| 8,223,924 B2* | 7/2012 | Borner et al. | 378/145 |
| 8,243,879 B2* | 8/2012 | Itoh | G21K 1/025 359/238 |
| 8,280,000 B2* | 10/2012 | Takahashi | 378/62 |
| 8,351,570 B2* | 1/2013 | Nakamura | G21K 1/06 378/145 |
| 8,374,309 B2* | 2/2013 | Donath et al. | 378/19 |
| 8,411,816 B2* | 4/2013 | Ohara | A61B 6/484 378/36 |
| 8,451,975 B2* | 5/2013 | Tada | A61B 6/4291 378/207 |
| 8,509,382 B2* | 8/2013 | Mukaide | A61B 6/032 378/51 |
| 8,532,252 B2* | 9/2013 | Nakamura | G21K 1/06 378/145 |
| 8,565,371 B2* | 10/2013 | Bredno | A61B 6/032 378/9 |
| 8,576,983 B2* | 11/2013 | Baeumer et al. | 378/62 |
| 8,591,108 B2* | 11/2013 | Tada | A61B 6/00 378/207 |
| 8,632,247 B2* | 1/2014 | Ishii | 378/207 |
| 8,755,487 B2* | 6/2014 | Kaneko et al. | 378/62 |
| 8,767,916 B2* | 7/2014 | Hashimoto | A61B 6/484 378/62 |
| 8,781,069 B2* | 7/2014 | Murakoshi | A61B 6/4233 378/36 |
| 8,824,629 B2* | 9/2014 | Ishii | 378/62 |
| 8,831,174 B2* | 9/2014 | Kohara et al. | 378/62 |
| 8,848,863 B2* | 9/2014 | Schusser et al. | 378/16 |
| 8,855,265 B2* | 10/2014 | Engel et al. | 378/62 |
| 8,903,042 B2* | 12/2014 | Ishii | A61B 6/4233 378/207 |
| 8,908,274 B2* | 12/2014 | Teshima | G21K 1/06 359/563 |
| 8,913,714 B2* | 12/2014 | Michel | A61B 6/484 250/370.09 |
| 8,989,353 B2* | 3/2015 | Kaneko | G21K 1/025 378/145 |
| 8,995,613 B2* | 3/2015 | Ouchi | G01N 23/046 378/62 |
| 9,001,969 B2* | 4/2015 | Murakoshi | A61B 6/4233 378/70 |
| 9,025,726 B2* | 5/2015 | Ishii | A61B 6/484 378/62 |
| 9,031,189 B2* | 5/2015 | Mukaide | G01N 23/04 378/53 |
| 9,036,773 B2* | 5/2015 | David | A61B 6/4035 378/36 |
| 9,046,466 B2* | 6/2015 | Ouchi | G01N 23/04 |
| 9,066,649 B2* | 6/2015 | Roessl | A61B 6/484 |
| 9,066,704 B2* | 6/2015 | Den | G01N 23/046 |
| 9,084,528 B2* | 7/2015 | Geller | A61B 6/00 |
| 9,105,369 B2* | 8/2015 | Koehler | A61B 6/032 |
| 9,107,637 B2* | 8/2015 | Ouchi | A61B 6/06 |
| 9,287,017 B2* | 3/2016 | Koehler | G21K 1/06 |
| 9,597,050 B2* | 3/2017 | Roessl | A61B 6/484 |
| 9,805,834 B2* | 10/2017 | Koehler | G21K 1/06 |
| 9,861,330 B2* | 1/2018 | Rössl | A61B 6/484 |
| 2012/0099702 A1 | 4/2012 | Engel et al. | |
| 2012/0250823 A1 | 10/2012 | Vogtmeier | |
| 2014/0177789 A1 | 6/2014 | Baturin et al. | |

FOREIGN PATENT DOCUMENTS

WO   WO2009101569   8/2009
WO   WO2010147125   12/2010

OTHER PUBLICATIONS

Wang et al, "Multiple Information Tomosynthesis With Grating-Based Phase-Contrast Imaging", Medical Imaging, Proceedings of SPIE, vol. 7258, 2009, p. 1-7.
"Grating Fabrication", Paul Scherrer Instit Grating Fabrication, http://www.psi.ch/lmn/grating-fabrication, Downloaded Nov. 17, 2014, p. 1-2.

* cited by examiner

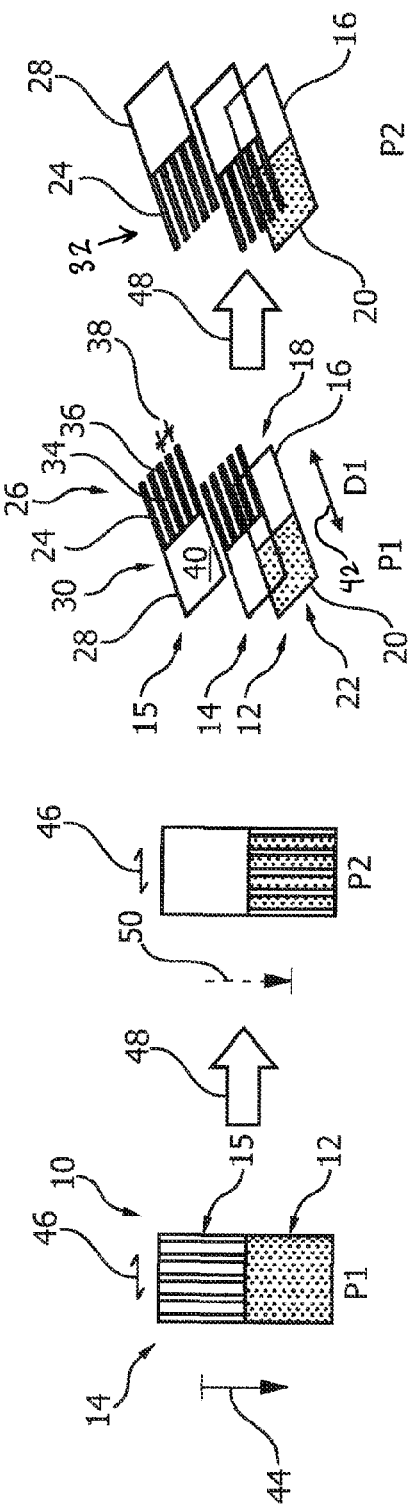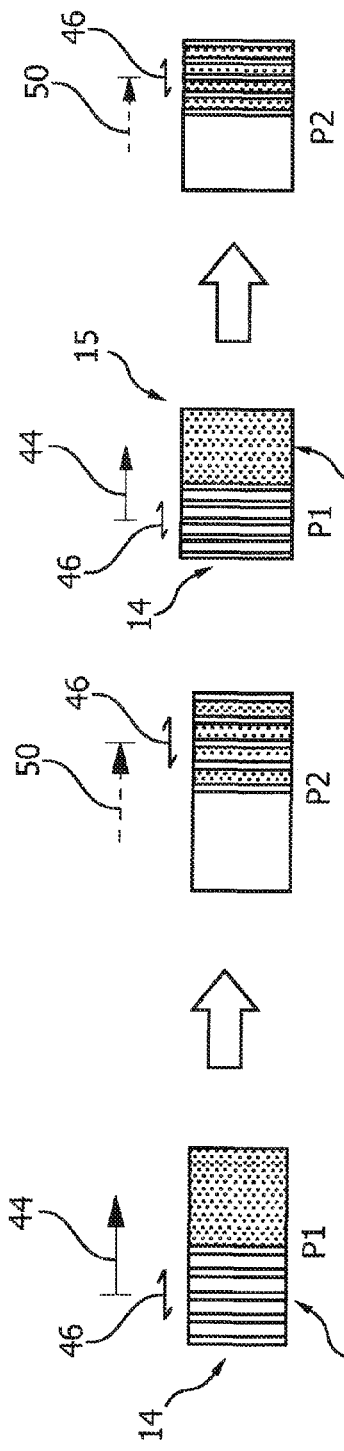

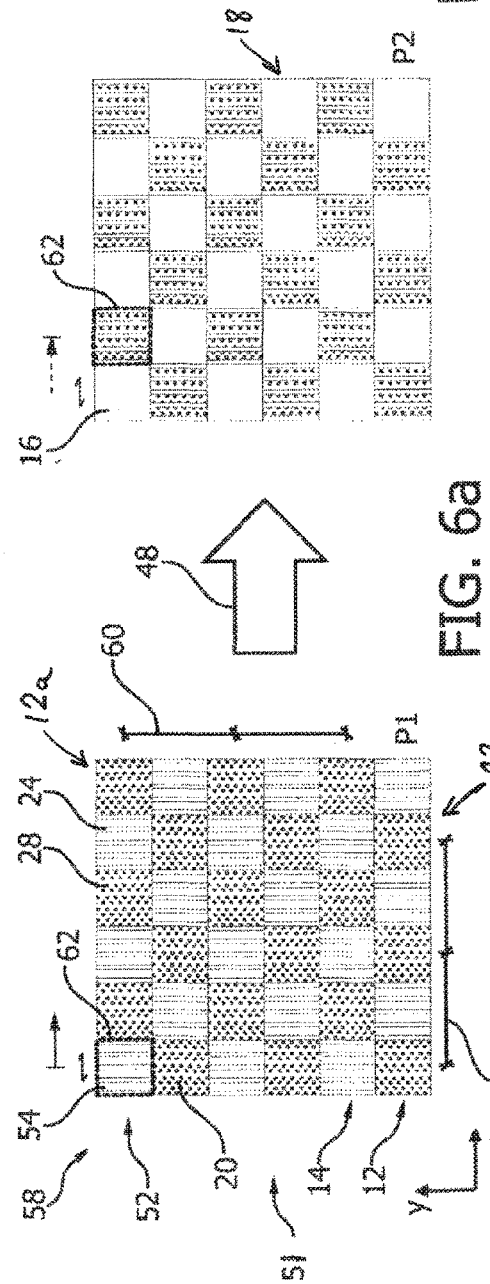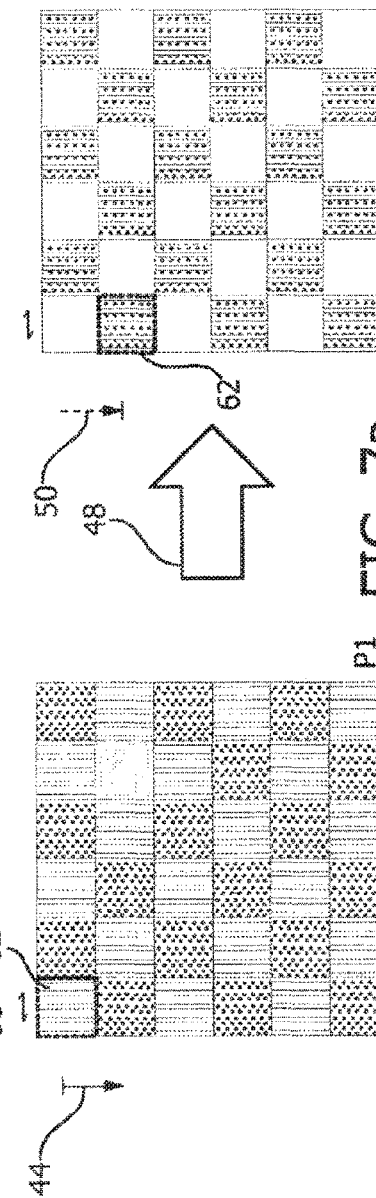
FIG. 6a  FIG. 6b
FIG. 7a  FIG. 7b

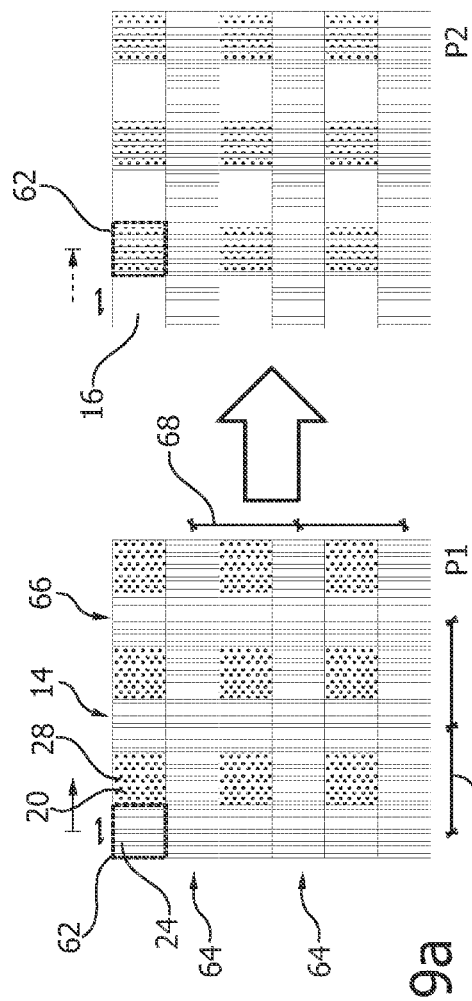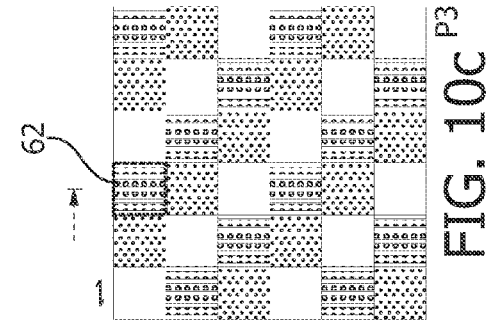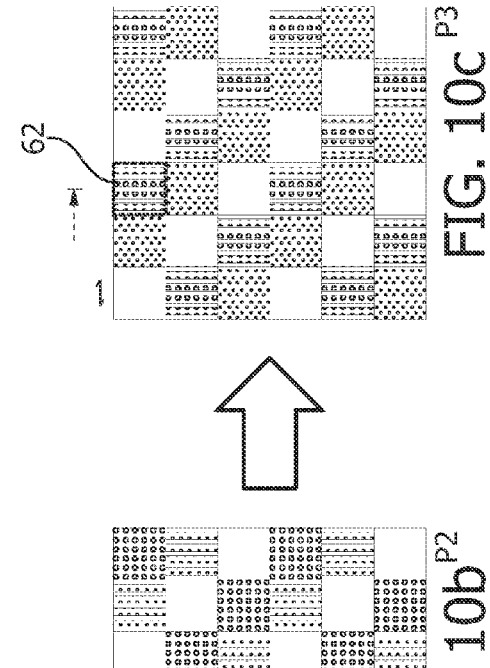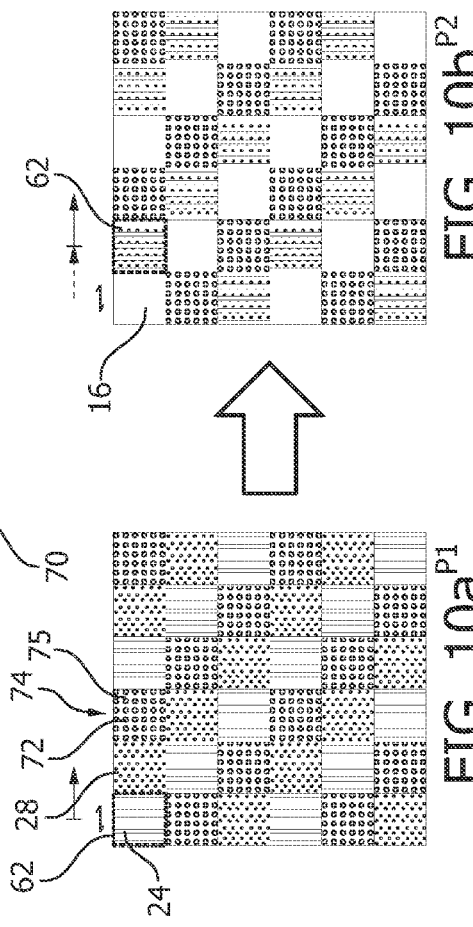

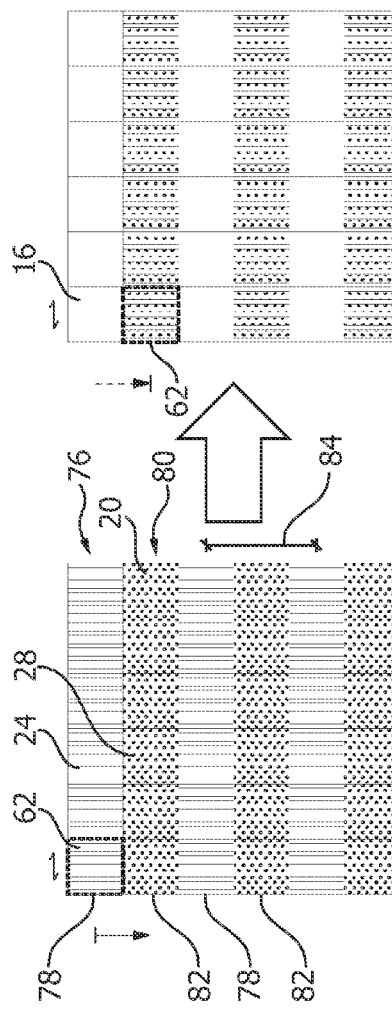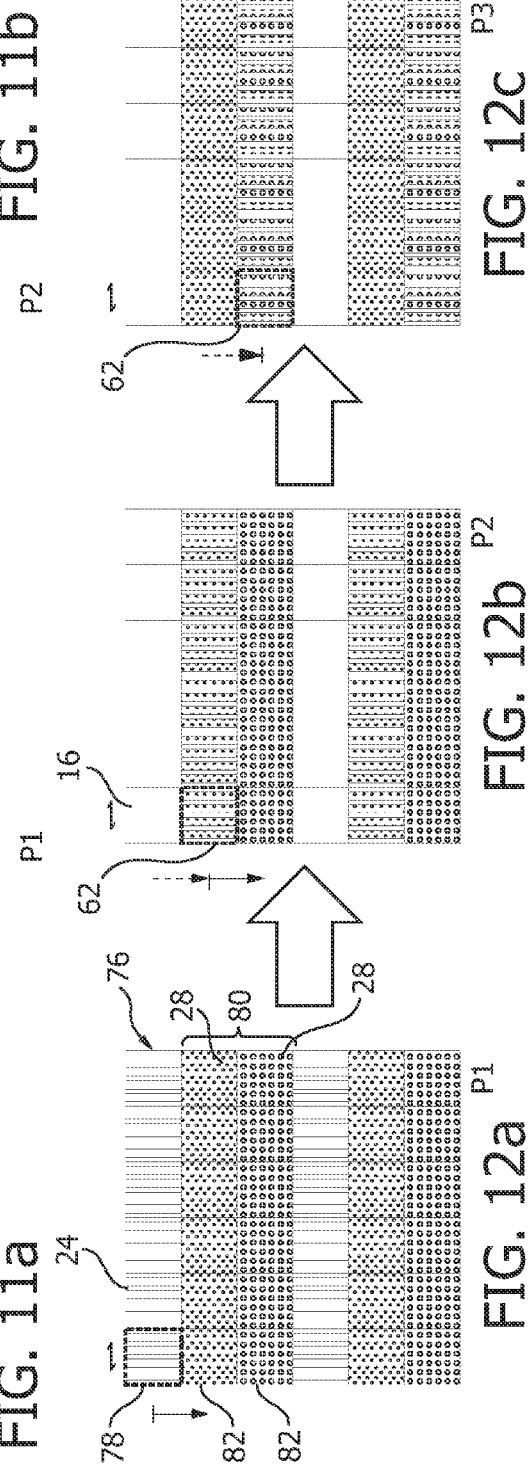

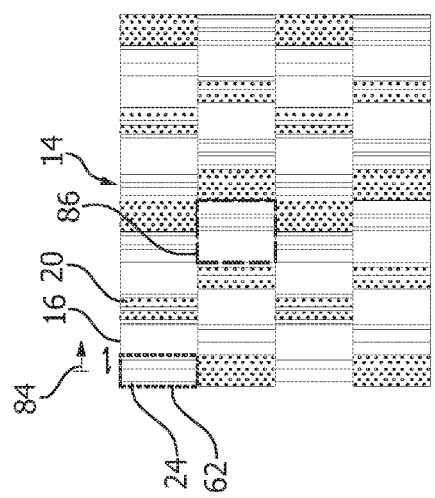
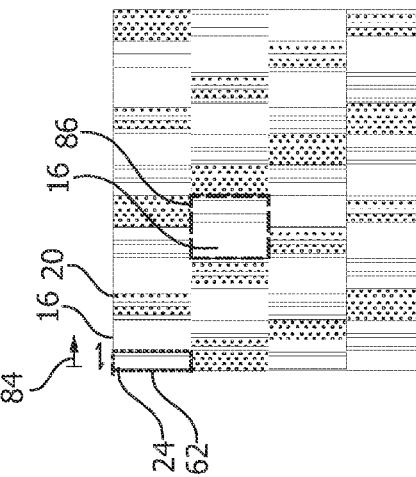
FIG. 13a FIG. 13b FIG. 14a FIG. 14b

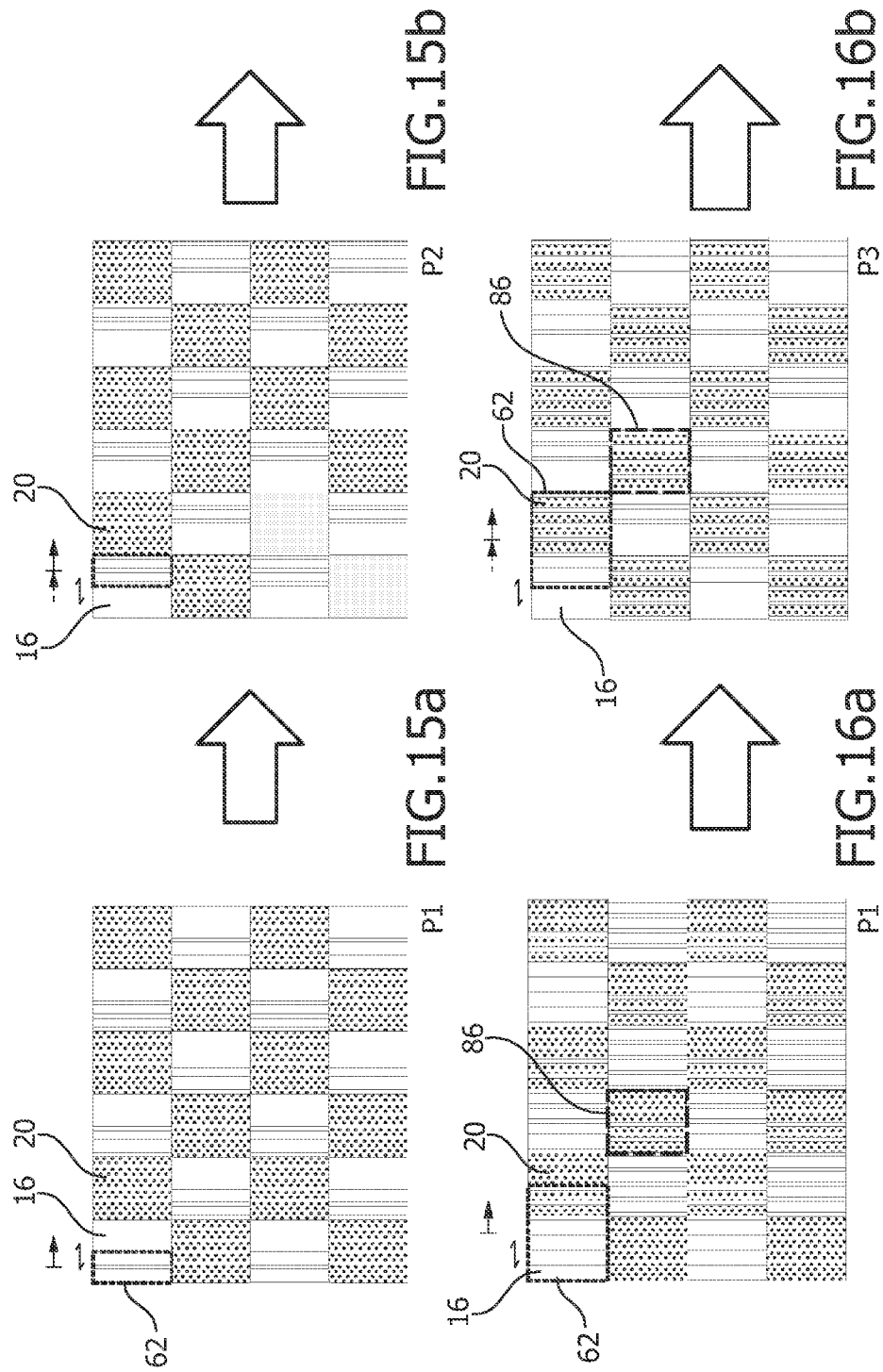

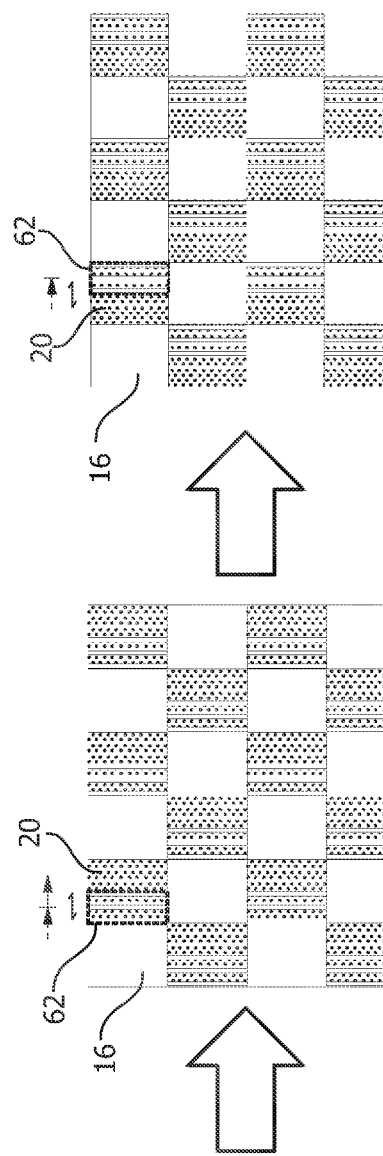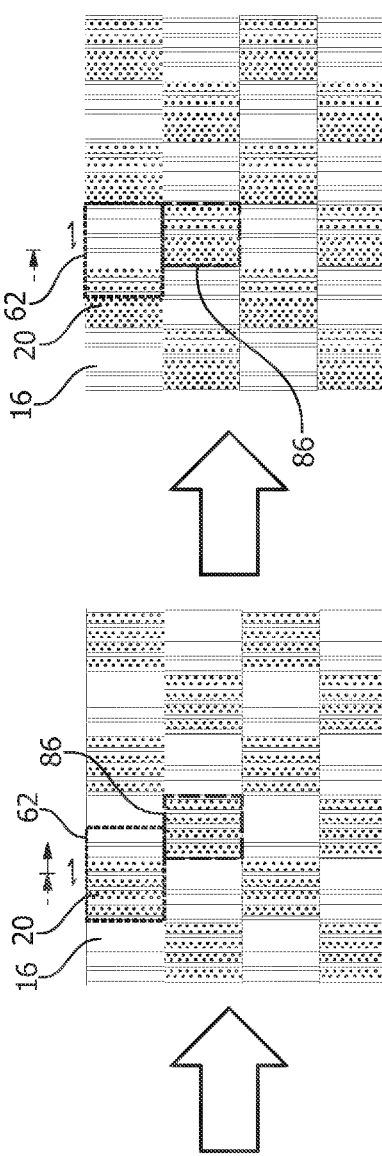

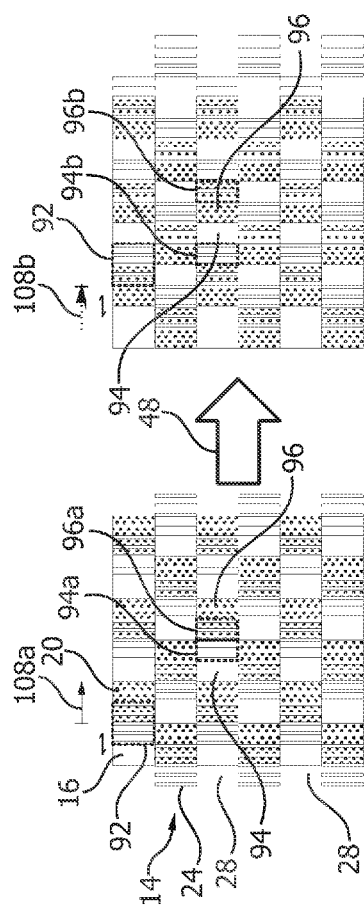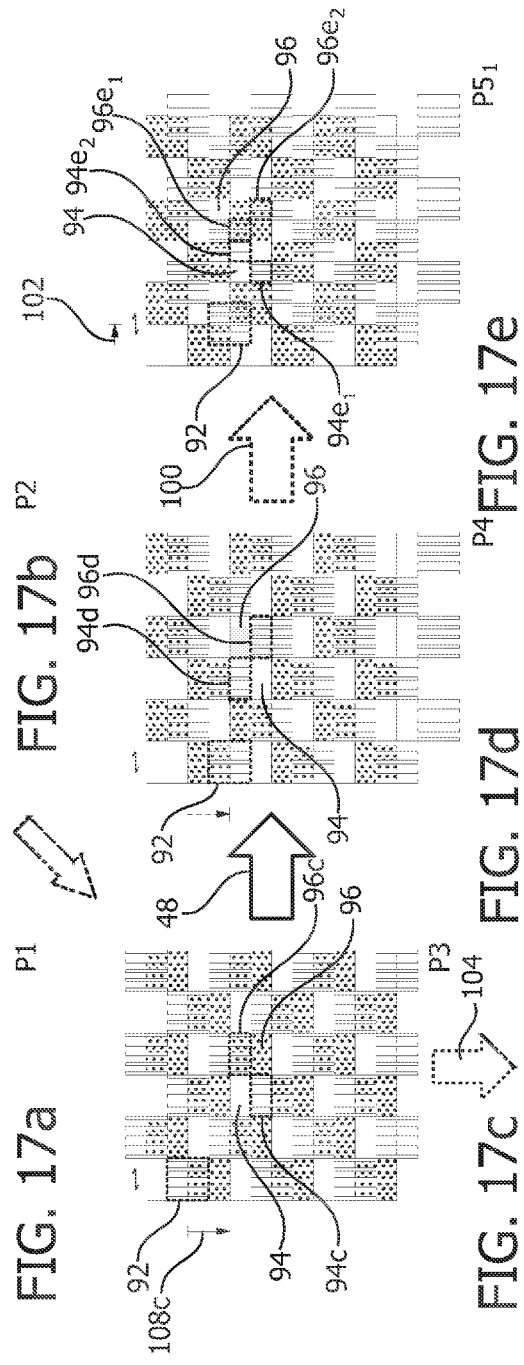

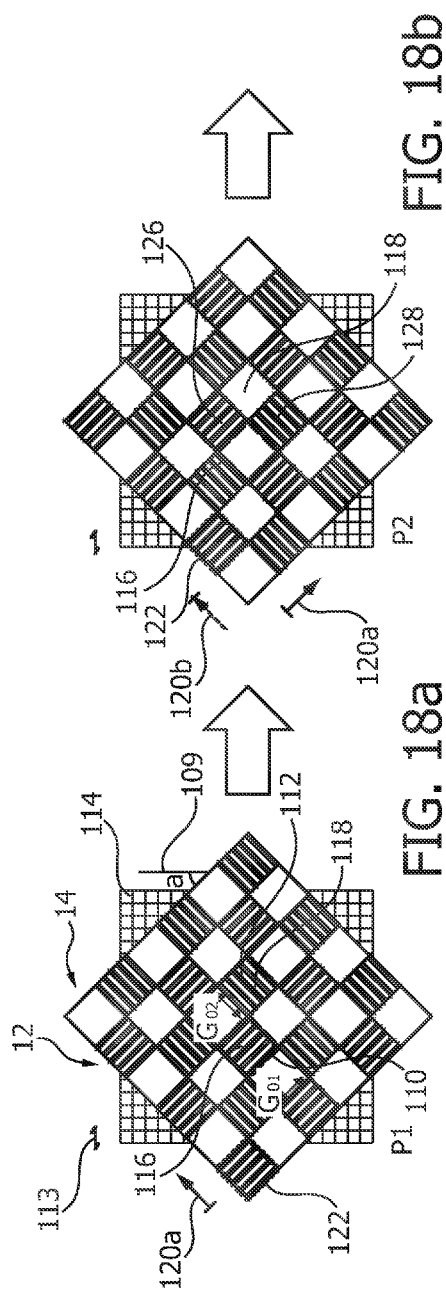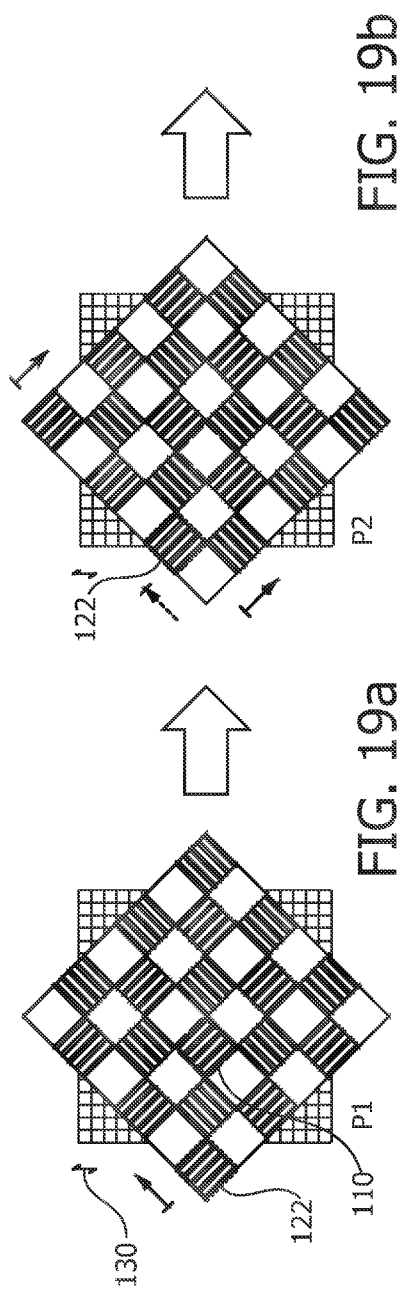

DIFFERENTIAL PHASE-CONTRAST IMAGING

FIELD OF THE INVENTION

The present invention relates to differential phase-contrast imaging, in particular to diffraction gratings for X-ray differential phase-contrast imaging, a detector arrangement of an X-ray system for generating phase-contrast images of an object, an X-ray image acquisition device for generating phase-contrast images of an object, a medical X-ray imaging system for differential phase-contrast imaging, a method for differential phase-contrast imaging as well as a computer program element and a computer-readable medium.

BACKGROUND OF THE INVENTION

Differential phase-contrast imaging is used, for example, to enhance the contrast of low absorbing specimen, compared to conventional amplitude contrast images. In EP 1 731 099 A1, an X-ray interferometer arrangement is described comprising a standard polychromatic X-ray source, a source grating, a beam splitter grating and an analyzer grating and an image detector. An object is arranged between the source grating and the beam splitter grating, i.e. the phase grating. By phase stepping the analyzer grating it is possible to record raw image data comprising phase information. The gratings, for example the phase grating and the analyzer grating, comprise a plurality of X-ray transparent slits between trenches of absorbing material, for example gold.

SUMMARY OF THE INVENTION

It has been shown that the amount of X-ray radiation being applied to the object, for example a patient, is partially absorbed by the analyzer grating and thus not completely used for recording image data by the sensor.

Hence, there may be a need to make better use of the X-ray radiation passing the object.

The object of the present invention is solved by the subject-matter of the independent claims, wherein further embodiments are incorporated in the dependent claims.

It should be noted that the following described aspects of the invention apply also for the diffraction grating, the detector arrangement, the X-ray image acquisition device, the medical X-ray imaging system, the method, the computer program and the computer-readable medium.

According to an exemplary embodiment of the invention, a diffraction grating for X-ray differential phase-contrast imaging is provided comprising at least one portion of a first sub-area and at least one portion of a second sub-area. The first sub-area comprises a grating structure with a plurality of bars and gaps being arranged periodically with a first grating pitch $P_{G1}$, wherein the bars are arranged such that they change the phase and/or amplitude of an X-ray radiation and wherein the gaps are X-ray transparent. The second sub-area is X-ray transparent and the at least one portion of the second sub-area provides an X-ray transparent aperture in the grating. Portions of the first and second sub-areas are arranged in an alternating manner in at least one direction.

According to the present invention, the term "changing phase" relates to shifting the phase of the X-ray radiation.

According to the present invention, the term "X-ray transparent" relates to the fact that X-ray radiation passing the grating is not changed in its phase, i.e. it is not phase shifted, and not changed in its amplitude, both to a measureable or reasonable amount.

According to a further exemplary embodiment, the diffraction grating is an analyzer grating for X-ray differential phase-contrast imaging.

According to a further aspect, the bars of the analyzer grating are X-ray absorbing such that they are changing the amplitude of X-ray radiation passing the grating.

According to a further exemplary embodiment, the diffraction grating is a phase grating for X-ray differential phase-contrast imaging.

According to a further aspect, the bars of the phase grating are changing the phase of X-ray radiation passing the grating.

According to a further exemplary embodiment, the portions of the first and second sub-areas are arranged across the area of the diffraction grating in a chessboard pattern.

According to a further exemplary embodiment of the invention, portions of the first sub-area are arranged linearly in at least one linear grating group comprising at least one line of portions of the first sub-area, and portions of the second sub-area are arranged linearly in at least one linear aperture group comprising at least one line of portions of the second sub-area. At least two linear grating groups and at least two linear aperture groups are provided and the linear grating groups and the linear aperture groups are arranged in an alternating manner in a first line pitch $P_{L1}$.

According to a further exemplary embodiment of the invention, the grating structure of the first sub-area comprises at least one first grating field and at least one second grating field; wherein a first grating orientation $G_{O1}$ of the first grating field is arranged in a first orientation and wherein a second grating orientation $G_{O2}$ of the second grating field is arranged in a second orientation which is transverse to the first orientation.

According to a further exemplary embodiment of the invention, a detector arrangement of an X-ray system for generating phase-contrast images of an object is provided comprising a first and a second diffraction grating and a detector with a sensor. The sensor comprises at least one sensor pixel of a first sub-group of pixels and at least one sensor pixel of a second sub-group of pixels. The first diffraction grating is a phase grating and the second diffraction grating is an analyzer grating. The analyzer grating and/or the phase grating are adapted to be stepped transversely in relation to the period of the analyzer grating. The phase grating and the analyzer grating are provided as a diffraction grating for X-ray differential phase-contrast imaging according to one of the above-mentioned exemplary embodiments. The first and second diffraction gratings are each adapted to be translated in relation to the sensor from a first position to at least a second position with a first translation pitch $P_{T1}$. The translation pitch $P_{T1}$ is adapted to the portions of the first and second sub-areas being arranged in the alternating manner in the at least one direction and in the first and second position, different fractions of the sensor are arranged behind the portions of the first and second sub-areas.

According to a further exemplary embodiment, further sensor pixels of further sub-groups are provided.

According to a further exemplary embodiment, an X-ray image acquisition device for generating phase-contrast images of an object is provided with an X-ray source, a source grating, a phase grating, an analyzer grating and a detector. The X-ray source generates an X-ray beam of polychromatic spectrum of X-rays. The source grating is adapted to provide sufficient transverse coherence to illuminate at least one full grating pitch of the phase grating coherently, so that interference can be observed at the location of the analyzer grating. The phase grating is illuminated by several of the slits and can be called a beam splitter grating as well as it splits the beam in the two leading orders, i.e. $1^{st}$ orders of diffraction, as the $0^{th}$ order is cancelled out exactly. The analyzer grating and/or the phase grating are adapted to be stepped transversely in relation to the period of the analyzer grating. The phase grating, the analyzer grating and the detector are provided as a detector arrangement according to one of the above-mentioned exemplary embodiments.

According to a further exemplary embodiment, a medical X-ray imaging system for differential phase contrast imaging is provided with the X-ray image acquisition device for generating phase-contrast images of an object according to the above-described embodiment. Further, a processing unit, an interface unit and an object receiving device are provided. The processing unit is adapted to control the X-ray source as well as the phase-stepping of the analyzer grating and/or the phase grating and the translation of the phase grating and the analyzer grating. The interface unit is adapted to provide the recorded first and second raw image data to the processing unit. The object receiving device is adapted to receive the object of interest for the phase contrast image acquisition.

According to a further exemplary embodiment, a method for differential phase contrast imaging is provided comprising the following steps: a1) Applying coherent X-ray radiation to an interferometer with two diffraction gratings in a first position, which diffraction gratings each comprise at least one grating part and at least an aperture part, wherein a first diffraction grating is a phase grating and a second diffraction grating is an analyzer grating. a2) Phase stepping the analyzer grating. a3) Recording first raw image data with a sensor with at least two parts; wherein a first and a second part are recording phase contrast image information and density information respectively. b) Translating the analyzer grating and the phase grating to a second position. c1) Applying coherent X-ray radiation to the interferometer in the second position. c2) Phase stepping the analyzer grating. c3) Recording second raw image data with a sensor with at least two parts, wherein the first and second part are recording density information and phase contrast information. d) Providing the recorded first and second raw image data as raw image data.

It is noted that the gratings part contain some intensity information, too. However, the distinction above refers more to the general difference for illustration.

According to a further exemplary embodiment of the invention, a method is provided, wherein step a1) comprises applying the coherent X-ray radiation to a phase grating and an analyzer grating, which each comprise at least one portion of a first sub-area. The first sub-area comprises a grating structure with a plurality of bars and gaps being arranged periodically with a first grating pitch $P_{G1}$. The bars are arranged such that they change the phase and/or amplitude of an X-ray radiation and the gaps are X-ray transparent. The phase grating and the analyzer grating also each comprise at least one portion of a second sub-area, which is X-ray transparent and wherein the at least one portion of the second sub-area provides an X-ray transparent aperture in the grating. Portions of the first and second sub-areas are arranged in an alternating manner in at least one direction. Further, step a3) comprises recording the first raw image data with the sensor in the first position, wherein the sensor comprises at least one sensor pixel of a first sub-group of pixels and at least one sensor pixel of a second sub-group of pixels. In the first position, the first sub-areas of the phase grating and the analyzer grating are each arranged at least partially in front of the first sub-group of pixels and the second sub-areas are arranged at least partially in front of the second sub-group of pixels. The first and second sub-groups are recording phase contrast image information and density information respectively. Further, step b) comprises translating the phase grating and the analyzer grating in relation to the sensor from the first position to at least the second position with a first translation pitch $P_{T1}$, wherein the translation pitch is adapted to the portions of the first and second sub-areas of the phase grating and the analyzer grating, being arranged in the alternating manner in the at least one direction. In the second position, the first sub-areas of the phase grating and the analyzer grating are each arranged at least partially in front of the second sub-group of pixels and the second sub-areas at least partially in front of the first sub-group of pixels. Further, step c3) comprises recording the second raw image data with the sensor in the second position, wherein the first and second sub-groups are recording density information and phase contrast image information respectively.

It can be seen as the gist of the invention to provide a diffraction grating with grating portions and aperture portions such that during one image acquisition step, phase-contrast image information can be recorded as well as density information. Thus, an increased degree of radiation passing the object, for example a patient, can be used for recording image data. As a further advantage, simply said, two different types of information, i.e. two different image types are recorded, namely phase-contrast image information as well as density information, e.g. conventional X-ray images. Of course, also the gratings portions provide some information about the mean attenuation, e.g. by averaging over the phase stepping scans. By translating the phase grating and the analyzer grating according to the invention to a second position, the analyzer grating having X-ray absorbing bars, those sensor areas or sensor pixels which have recorded phase information in the first acquisition step are now covered with the aperture portions such that these pixels can now record density information, whereas the pixels that have recorded density information in the first acquisition step are now able to record phase-contrast image information in the second acquisition step. As an example, in case of a common analyzer grating with a grating structure across the whole grating area, wherein the bars cover 50% of the area and the gaps thus provide 50% of the area to be non-absorbing, only 50% of the X-ray dose reaching the analyzer grating is actually recorded by the sensor. The other 50% are absorbed by the analyzer grating. In case of the diffraction grating according to the invention, if the grating sub-area comprises 50% of the diffraction grating area and thus the aperture sub-area comprises 50% of the diffraction grating area, and assuming the same bars/gap ratio of 50%, as before, the diffraction grating according to the invention only absorbs 25% of the radiation hitting the diffraction grating. This is because in 50% of the area, the portions of the aperture sub-area do not absorb the X-ray radiation and in the rest of the 50% with portions of the grating sub-area, only 50%, i.e. 25% of the overall doses, is absorbed by the bars.

These and other aspects of the present invention will become apparent from and elucidated with reference to the exemplary embodiments described hereinafter.

BRIEF DESCRIPTION OF THE DRAWINGS

Exemplary embodiments of the invention will be described in the following with reference to the following drawings.

FIG. 3a and 3b schematically show a detector arrangement with a diffraction grating according to the invention.

FIGS. 4-5 show further exemplary embodiments of the detector arrangement of FIG. 3.

FIGS. 6a, 6b, 7a, 7b, 8a, 8b, 9a, 9b, 10a-c, 11a, 11b, 12a-12c, 13a, 13b, 14a, 14b, 15a-d, 16a-d, and 17a-f show further exemplary embodiments of detector arrangements according to the invention.

FIGS. 18a-d and 19a-d show further exemplary embodiments of detector arrangements according to the invention.

DETAILED DESCRIPTION OF EMBODIMENTS

Figure 1:
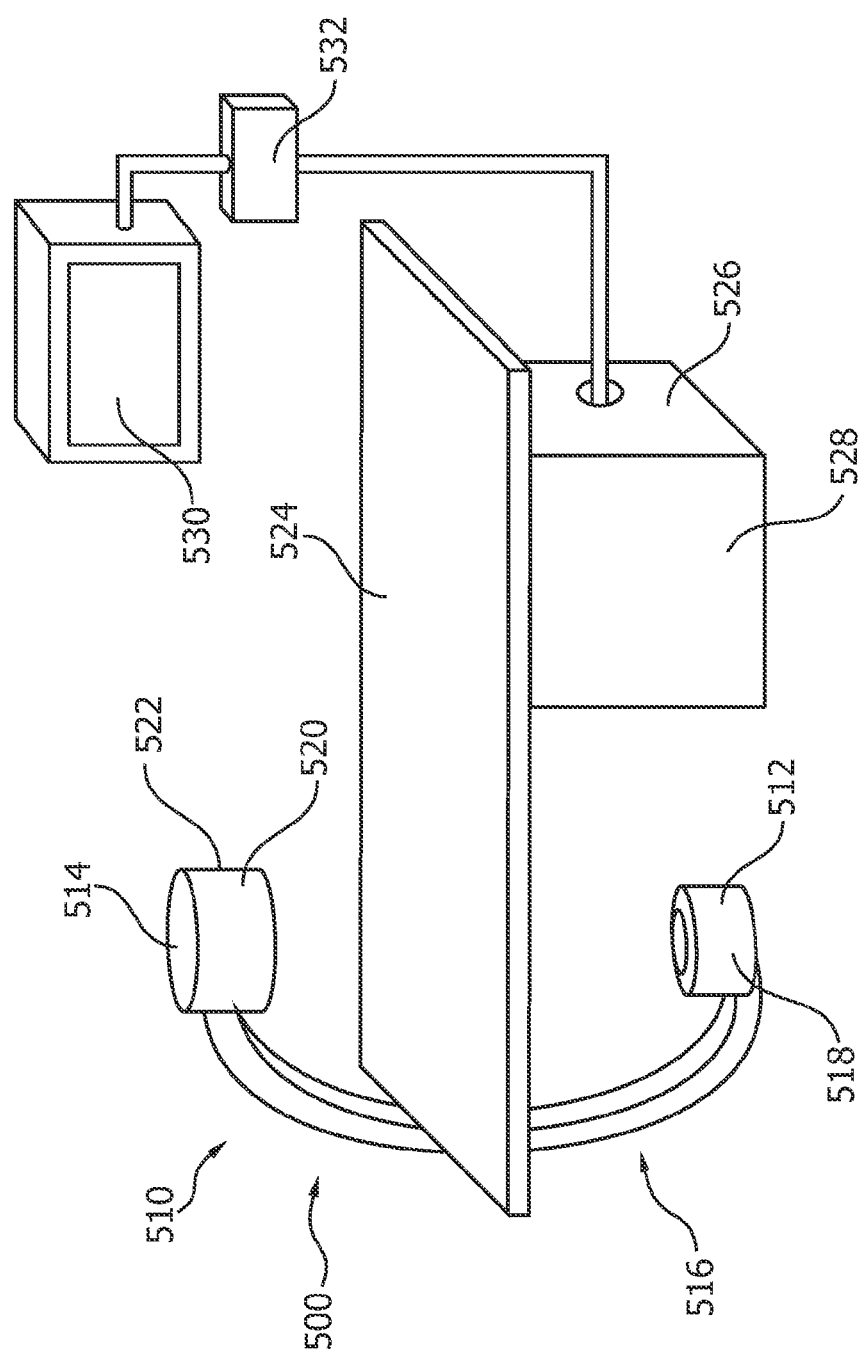
FIG. 1 schematically shows an example of a medical X-ray imaging system according to the invention.

FIG. 1 schematically shows a medical X-ray imaging system 500 for differential phase-contrast imaging. The system comprises an X-ray image acquisition device 510 for generating phase-contrast images of an object, for example a patient. The X-ray image acquisition device 510 comprises an X-ray source 512 and a detector 514 arranged opposite to the X-ray source 512 on a C-arm structure 516. Further, the X-ray image acquisition device 510 comprises a source grating 518 (not further shown), a phase grating 520 and an analyzer grating 522 which are also not further shown. These aspects will be described in more detail with reference to FIG. 2 below.

A table 524 is provided as an object receiving device. The table 524 is arranged at least partially between the X-ray source 512 and the detector 514.

Further, a processing unit 526 and an interface unit 528 (not further shown) are also provided. Still further, a display device 530 is arranged above the table 524 to display information to the user. Further, an interaction panel 532 is arranged for input by the user.

The processing unit 526 is located underneath the table 524 to save space within the examination room. Of course, it is also possible to locate the processing unit 526 at a different place, for example a different room.

It is noted that the example shown is of a so-called C-type X-ray image acquisition device 510 comprising an arm 516 in form of a C where the image detector 514 is arranged at one end of the C-arm 516 and the source 512 of X-ray radiation is located at the opposite end of the C-arm 516. The C-arm 516 can be movably mounted and can be rotated around the object of interest located on the table 524. In other words, it is possible to acquire images with different directions of view.

It is further noted, that, of course, other forms of X-ray image acquisition devices are also possible, such as a gantry with a rotating pair of X-ray source and detector.

According to an exemplary embodiment, the processing unit 526 is adapted to control the X-ray source 512 as well as phase stepping of the analyzer grating 522 and/or the phase grating 520 and translating the phase grating 520 and the analyzer grating 522, which will be explained further below.

The interface unit 528 is adapted to provide the recorded data by the detector 514 to the processing unit 526.

Figure 2:
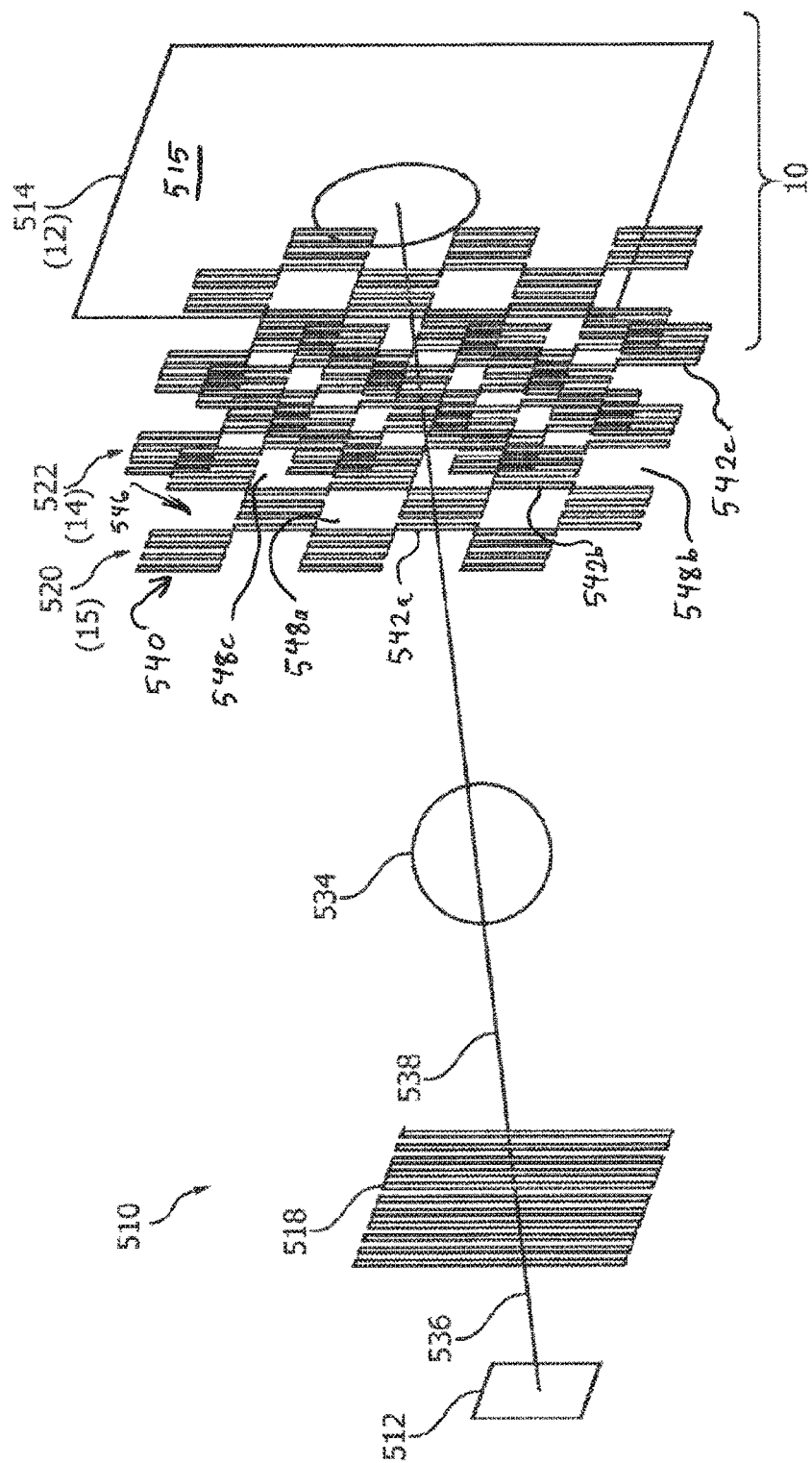
FIG. 2 schematically shows an X-ray image acquisition device for generating phase-contrast images according to the invention.

The X-ray image acquisition device 510 will now be described with reference to FIG. 2. The X-ray image acquisition device 510 for generating phase-contrast images comprises: the X-ray source 512; the source grating 518; the phase grating 520; the analyzer grating 522; and the detector 514, with a sensor 515, for examination of an object, indicated with reference numeral 534. An X-ray beam 536 of polychromatic spectrum of X-rays is provided by the X-ray source 512 which is provided as a conventional X-ray source. The X-ray radiation beam 536 is applied to the source grating 518. The source grating 518, also referred to as G0, is adapted to provide sufficient transverse coherence to illuminate at least one full grating pitch of the phase grating 520 coherently, so that interference can be observed at the location of the analyzer grating 522. Simply said, the source grating 518 is "splitting" the X-ray radiation such that coherent X-ray radiation is provided (not further shown). The beam 536 passing the source grating 518 is indicated with reference numeral 538. The phase grating 520 is illuminated by several of the slits and can be called a beam splitter grating as well as it splits the beam 538 in the two leading orders, i.e. $1^{st}$ orders of diffraction, as the $0^{th}$ order is cancelled out exactly. Passing the phase grating 520, the split beams hit the analyzer grating 522 in an analyzer plane. After recombining the split beams behind the phase grating 520, the recombined beam is applied to the analyzer grating 522. Then, the detector 514 with a sensor is recording raw image data while the analyzer grating 522 is stepped transversely in relation to one period of the analyzer grating 522. The phase grating 520, the analyzer grating 522 and the detector 514 are provided as a detector arrangement 10 according to the invention, which will be described in the following. The analyzer grating 522 and/or the phase grating 520 are adapted to be stepped transversely at least in relation to the period of the analyzer grating 522. Further, the phase grating 520 and the analyzer grating 522 are provided as a diffraction grating for X-ray differential phase-contrast imaging according to one of the embodiments described below.

The phase grating 520 may be made up of two sub-areas, arranged together in a chess-board pattern. A first sub-area 540 may include, throughout, a grating structure of bars and gaps. The first sub-area 540 may spatially correspond to the chess-board squares of a same color, each such square spatially corresponding to a portion 542a, 542b, 542c, ... of the first sub-area. A second sub-area 546 may spatially correspond to the chess-board squares of the other color, and may consist of portions 548a, 548b, 548c, ... that are X-ray transparent. Thus, the phase grating 520 may consist of collectively: a) the portions 542a, 542b, 542c, ... of the first sub-area 540; and b) the portions 548a, 548b, 548c, ... of the second sub-area 546. The analyzer grating 522 may be configured the same way, as seen in FIG. 2.

According to a further aspect, also the phase grating 520, also referred to as G1, is stepped with respect to the analyzer grating 522, referred to as G2. Then however, it suffices to step the phase grating 520 by only ½ of its pitch, as the frequency of the interference fringes at the analyzer grating 522 is double the pitch of G1, i.e. the phase grating, which is the case for parallel beams. For cone beams, a magnification leads to a slight deviation from the factor 2.

The first and second diffraction gratings are each adapted to be translated in relation to the sensor from a first position P1 to at least a second position P2 with a first translation pitch $P_{T1}$, which is adapted to the portions of the first and second sub-areas being arranged in the alternating manner in the at least one direction. In the first and second position, different fractions of the sensor are arranged behind the portions of the first and second sub-areas.

According to another aspect, the source grating 518 is provided as an absorption grating as well, since the Talbot effect is observable here, too.

According to an exemplary embodiment, the sensor comprises at least one sensor pixel of a first sub-group of pixels and at least one sensor pixel of a second sub-group of pixels (see below).

In FIGS. 3a and 3b, the detector arrangement 10 of an X-ray system for generating phase-contrast images of an object is schematically shown. The detector arrangement 10 comprises a detector 12 with a sensor and a first and second diffraction grating, which are provided as an analyzer grating 14 and a phase grating 15, as already described above. FIG. 3a shows a plan view and FIG. 3b shows an isometric view.

With relation to the direction of radiation to be applied, the phase grating 15 and the analyzer grating 14 are arranged in front of the detector 12 according to the following figures, wherein the phase grating 15 is arranged in front of the analyzer grating 14.

For a better understanding, FIG. 3b shows a perspective view of the schematic arrangement. In FIG. 3a, the analyzer grating 14 is arranged above the detector 12 and the phase grating 15 above the analyzer grating 14.

It is explicitly noted that in the following, the analyzer grating 14 is described. However, according to the present invention, the grating features of analyzer grating 14 are also provided for the phase grating 15. Further, the phase grating 15 and the analyzer grating 14 are arranged in front of each other with the same (sub-) grating structure according to one of the embodiments described for the analyzer grating, in order to provide the detection of phase-gradient information.

In other words, the features and characteristics described for the analyzer grating 14 also apply to the phase grating 15, which is not further shown for a better understanding of the drawings.

As can be seen, a sensor of the detector 12, (said sensor being disposed behind the analyzer grating 14 in FIG. 6a, but partially visible in FIG. 6a, for example through the top rightmost portion of the analyzer grating portions shown—said sensor likewise being disposed behind the right-shifted analyzer grating 14 in FIG. 6b, but partially visible in FIG. 6b, for example through the top leftmost portion of the analyzer grating portions shown), comprises at least one sensor pixel 16 of a first subgroup of pixels 18 (see also FIG. 6ff.) and at least one sensor pixel 20 of a second subgroup of pixels 22 (see also FIG. 6ff.). The analyzer grating 14 for X-ray differential phase-contrast imaging comprises at least one portion 24 of a first sub-area 26 and at least one portion 28 of a second sub-area 30—these sub-areas 26, 30 are better seen in FIG. 2 as, for example, the sub-areas 540, 546 in a chess-board pattern. The first sub-area 26 comprises a grating structure 32 with a plurality of bars 34 and gaps 36 being arranged periodically with a first grating pitch $P_{G1}$ 38, as seen in FIG. 3b. (Likewise, with reference to FIG. 8a, bar-and-gap patterned portions 24, here rectangular rather than square-shaped, and the first sub-area 26 comprising them, are shown.) The bars 34 are arranged such that they change the phase and/or amplitude of an X-ray radiation and the gaps 36 are X-ray transparent. The second sub-area 30 is X-ray transparent and the at least one portion 28 of the second sub-area 30 provides an X-ray transparent aperture 40. Portions of the first and second sub-areas 26, 30 are arranged in an alternating manner in at least one direction D1 42. The analyzer grating 14 is adapted to be translated in relation to the sensor 515 from a first position P1 to at least a second position P2 with a first translation pitch $P_{T1}$, indicated with an arrow 44. The translation pitch $P_{T1}$ is adapted to the portions of the first and second sub-areas 26, 30 being arranged in the alternating manner in the at least one direction. In the first and second position P1, P2, different fractions 12a of the sensor 515 are arranged behind the portions of the first and second sub-areas.

According to a further aspect, the diffraction grating is an analyzer grating for X-ray differential phase-contrast imaging, wherein the bars of the analyzer grating are X-ray absorbing such that they are changing the amplitude of X-ray radiation passing the grating.

According to a further exemplary embodiment, the diffraction grating is a phase grating for X-ray differential phase-contrast imaging, wherein the bars of the phase grating are changing the phase of X-ray radiation passing the grating.

According to a further aspect, the sensor is adapted to record raw image data.

According to a further aspect, the analyzer grating 14 is adapted to be phase-stepped transversely in relation to one period of the analyzer grating structure with the first grating pitch $P_{G1}$ 32.

As can be seen, in FIG. 3a, the translation direction is indicated by the virtual arrow 44. The phase stepping is indicated with a smaller double arrow 46 perpendicular to the grating structure. As can be seen, the analyzer grating 14 is translated in a vertical direction from the first position which is shown in the left half of FIG. 3a, to the second position which is shown in the right half of FIG. 3a. The process of translation is indicated with a broad arrow 48. The arrow 44 in the left half of FIG. 3a indicates that this step of translating will be applied during the translation. Following, since in the state shown in the right half, the translation has already been applied, an arrow in a broken line 50 is indicating the preceding translation step, i.e. the step that has been performed.

It is noted that the arrow 44 indicating a translation step to be performed and the arrow 50 indicating a preceding translation step, i.e. a translation step that has been performed, are used throughout the following figures and will thus not be explicitly mentioned at all instances where this is shown in the drawings. However, it is noted that these symbols are shown and explained in such a clear manner that they are clear to a skilled person and thus need no further explanation in the written description.

In FIG. 3b, the translation from the first position P1 to the second position P2 is shown in a perspective view.

Of course, all figures are not shown in scale. Especially the grating structures and the distances of the gratings in the perspective illustrations are only shown schematically.

As can be seen in FIG. 4, according to a further aspect of the invention, the analyzer grating 14 and the detector 12 can be arranged such that the translation occurs horizontal, i.e. perpendicular to the grating structure. Of course, the (effective) phase stepping, indicated by double arrow 46, has to take place perpendicular to the grating structure.

As can be seen from FIG. 5, the portions of the first and second sub-areas 26, 30 can be provided to be rectangular, wherein their extension in one direction differs from the extension in a second direction. Alternatively, as shown in FIGS. 3 and 4, the portions each have a square form.

According to a further (not shown) aspect of the invention, the grating-portions, i.e. portions of the first sub-area, and the aperture-portions, i.e. portions of the second sub-area, are provided in different shapes such as triangular, hexagon or others.

As can be seen by these very schematic illustrations, with the analyzer grating 14 according to the invention, it is possible to acquire image data in a first step where the first subgroup 18 of pixels records phase gradient information, since the grating part, i.e. the first sub-area 26, is arranged above or in front of it with respect to the direction of radiation. The second subgroup of pixels 22 records image data comprising density information since the analyzer grating 14 is arranged such that the second sub-area 30, or in other words the X-ray transparent aperture 40, is arranged in front of this part of the sensor.

Due to the translation, indicated with arrow 48, the analyzer grating 14 is then positioned such that the grating part, i.e. the first sub-area 26 is arranged in front of the second subgroup of pixels 22, i.e. in FIGS. 3 to 5 the at least one sensor pixel 20 of the second subgroup of pixels 22, such that this sensor pixel 20 now records image data comprising phase gradient information. The second sub-area 30 is now arranged in front of the at least one sensor pixel 16 of the first subgroup 18 of pixels, thus recording density information in this second acquisition step. Of course, for recording phase gradient information, the analyzer grating 14 is adapted to be phase-stepped in the first and the at least second position P1, P2.

According to a further aspect of the invention, in the first and second position P1, P2, one of the first or second sub-areas 26, 30 of the analyzer grating 14 is arranged in front of one of the first or second subgroups of pixels 18, 22, and in the second position P2, the other one of the first or second sub-areas 26, 30 of the analyzer grating 14 is arranged in front of the other one of the first or second subgroup of pixels 18, 22, which is not further shown.

According to a further aspect, in the first and/or second position P1, P2, the at least one portion of the first or second sub-area 26, 30 is arranged partially in front of one of the first or second subgroups of pixels 18, 22.

According to a further aspect of the invention, portions of the first and second sub-areas 26, 30 are arranged in an alternating manner in a first and a second direction. For example, the first direction is referred to as the x-direction and the second direction is the y-direction.

According to a further aspect, a plurality of the portions of the first sub-area is arranged in the x-direction with a first x repetition pitch $P_{R1x}$.

According to a further aspect, a plurality of the portions of the first sub-area is arranged in the y-direction with a first y repetition pitch $P_{R1y}$.

According to a further aspect, a plurality of the portions of the second sub-area is arranged in the x-direction with a second x repetition pitch $P_{R2x}$.

According to a further aspect, a plurality of the portions of the second sub-area is arranged in the y-direction with a second y repetition pitch $P_{R2y}$.

According to a further aspect, the first x repetition pitch $P_{R1x}$ and the second x repetition pitch $P_{R2x}$ are equal.

According to a further aspect, the first y repetition pitch $P_{R1y}$ and the second y repetition pitch $P_{R2y}$ are equal.

According to a further aspect, the x and y repetition pitches $P_{Rx}$, $P_{Ry}$ are equal.

It must be noted that the above-mentioned aspects can be freely combined.

According to a further aspect, the portions of the first and second sub-areas 26, 30 are equal in size. With reference to FIGS. 6a and 6b, the portions of the first and second sub-areas 26, 30 are arranged across the area of the analyzer grating 14 in a chessboard pattern 51. As schematically illustrated, a plurality of portions 52 of the first sub-area 26, i.e. portions with a grating structure indicated with a linear line structure 54 throughout the figures, are arranged in the horizontal direction, i.e. the x-direction with a first x repetition pitch $P_{R1x}$ indicated with reference numeral 56. Further, a plurality of the portions 58 of the first sub-area 26 are arranged in the y-direction with a first y repetition pitch $P_{R1y}$, indicated with reference numeral 60. As can be seen, the first repetition pitches are equal in size.

Underneath the analyzer grating 14, the detector 12 is arranged. The sensor comprises sensor pixels 16 of the first subgroup 18 of pixels, which are covered by the portions of the first sub-area 26 of the analyzer grating 14. The sensor further comprises sensor pixels 20 of the second subgroup of pixels 22 which are indicated with a dotted-line pattern which pattern is only for explanation and is not referring to any structural difference of the sensor pixels of the first and second subgroup. FIG. 6a shows the first position P1 in which raw image data can be recorded by the sensor. As mentioned above, the sensor pixel 16 of the first subgroup 18 of pixels records phase gradient information (of course, together with some density information; see above) whereas the sensor pixels 20 of the second subgroup of pixels 22 records density information at this position, while phase-stepping is applied.

By translating the analyzer grating 14, the portions 24 of the first sub-area 26 are arranged in front of the sensor pixels 20 of the second subgroup of pixels 22.

The sensor pixel 16 of the first subgroup 18 of pixels is now arranged behind the portions 28 of the second sub-area 30. Thus, in the second position P2, as shown in FIG. 6b, the sensor pixels 16 of the first subgroup 18 record density information whereas the sensor pixels 20 of the second subgroup of pixels 22 now record phase gradient information.

The translation of the analyzer grating 14 is indicated with a thick frame 62 indicating a particular portion with a grating structure of the first sub-area 26. However, the frame 62 is for illustrative purposes only.

In FIGS. 6a and 6b, the analyzer grating 14 has been translated with relation to the sensor in a horizontal way, wherein the sensor remains. Further, it must be noted that the illustrations show a section of a diffraction grating (phase grating/analyzer grating) according to the invention, which can be seen in that, although moving the analyzer grating 14 from FIG. 6a to FIG. 6b by one pitch to the right, the left column of FIG. 6b is also shown with grating fields.

According to a further aspect of the invention, it is also possible to translate the analyzer grating 14 in another direction, i.e. in the vertical direction as indicated by the translating arrows 44, 50. This is illustrated by the frame 62 moving downwards one pitch when translating the analyzer grating 14. Since the features described in relation with FIGS. 6a and 6b remain except for the translation direction, the reference numerals are not repeated in FIGS. 7a and 7b.

Figure 8B:
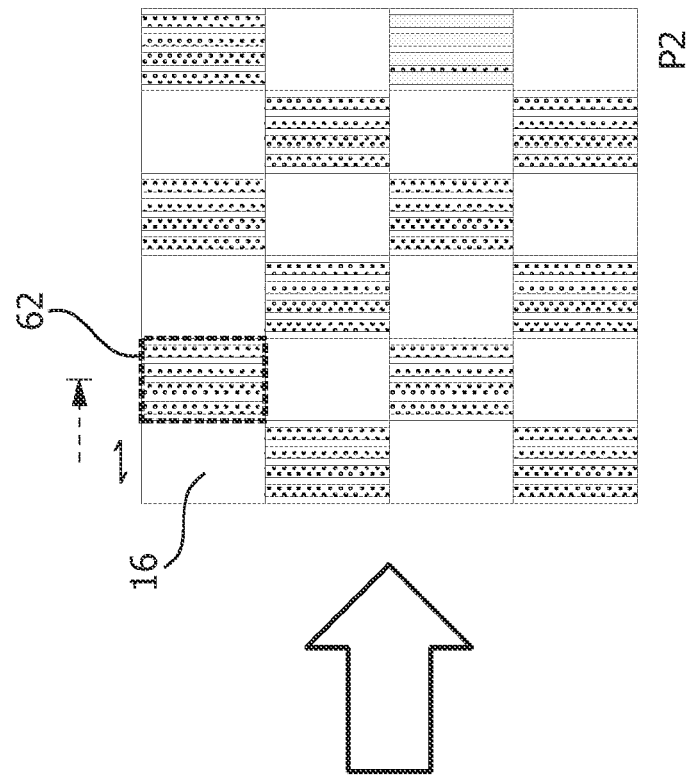
Figure 8A:
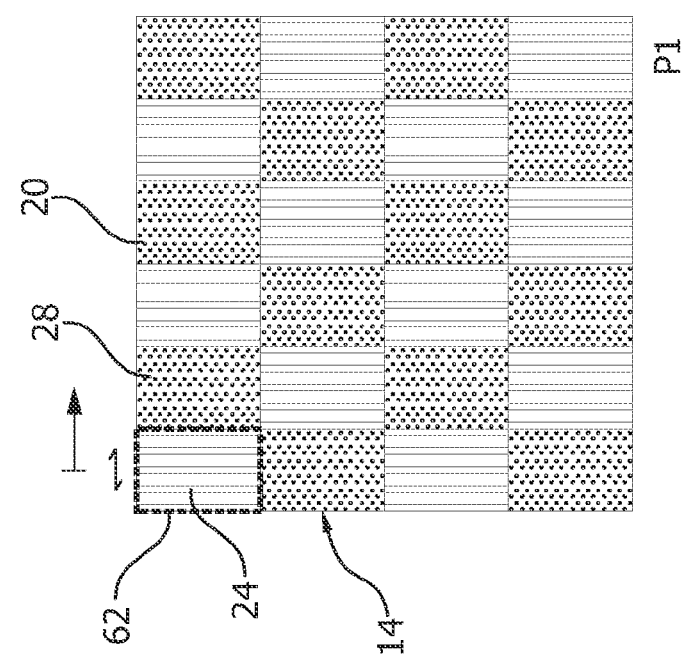

As shown in FIGS. 8a and 8b, the chessboard pattern 51 can also be arranged with rectangular fields. As can be seen, the portions 24, 28 of the first and second sub-areas 26, 30 are rectangular, wherein the extension in one direction differs from the extension in a second direction.

According to a further aspect (not shown), the analyzer grating 14 of FIGS. 8a and 8b can also be moved in the vertical direction instead of the horizontal translation shown in FIG. 8a and FIG. 8b.

According to a further aspect of the invention, illustrated in FIGS. 9a and 9b, a number of portions of the first and/or second sub-areas are arranged adjacent as first subsets 64 and/or second subsets 66. The first and/or second subsets are arranged across the area of the analyzer grating in a first subset repetition pitch $P_{SR1}$ indicated with reference numeral 68 and/or second subset repetition pitch $P_{SR2}$ (indicated with reference numeral 70) in at least one direction respectively. As can be seen in FIG. 9, the subset repetition pitches $P_{SR}$ are equal. However, of course it is also possible to provide different repetition pitches.

According to the example shown in FIG. 9, a pattern results with open fields in the analyzer grating 14, i.e. with portions 28 of the second sub-area 30 that are provided only in every second field, across the horizontal direction as well as in the vertical direction. By translating the analyzer grating 14 by one translation pitch in the horizontal direction, the apertures 40 provided by the portions 28 of the second sub-area 30 are now arranged above or in front of the adjacent pixels of the sensor which belong to the second subgroup of pixels 22.

As can be seen, density information is thus recorded in every second horizontal line. The other lines in between record phase gradient information data in the first position as well as in the second position. However, by computational steps it is possible to compute the so to speak missing pixels of the X-ray image based on the density information.

According to a further aspect, measurements are repeated after a shift in the y-direction (not shown).

According to a further aspect, a first number of portions of the first sub-area and a second number of portions of the second sub-area are arranged across the analyzer grating in an alternating manner in two directions. As can be seen from FIG. 10, a field with a grating structure is provided only in every third field with respect to the horizontal direction and only in every third field with respect to the vertical direction. From column to column, the grating fields are displaced in diagonal direction by one pitch. In order to acquire phase gradient information for all sensor pixels, in case the sensor pixels are equal with the portion size of the first and second sub-areas of the analyzer grating 14, it is necessary to provide three acquisition steps as indicated by FIGS. 10a, 10b and 10c. As indicated by the frame 62, the analyzer grating 14 is arranged in a first position P1 in FIG. 10a and then translated by a first translation step to a second position in FIG. 10b. Next, the analyzer grating 14 is translated in a second translation step to a third position P3 shown in FIG. 10c.

In such a case, the sensor comprises pixels 72 of a third subgroup of pixels 74 which are indicated with a second dotted-line pattern 75 for illustrational purposes. With respect to a particular pixel, by providing three acquisition steps, the pixel records phase gradient data in one acquisition step and density information in two acquisition steps.

According to a further aspect of the invention, portions of the first sub-area 26 are arranged linearly in at least one linear grating group 76 comprising at least one line 78 of portions 24 of the first sub-areas. Portions 28 of the second sub-area 30 are arranged linearly in at least one linear aperture group 80 comprising at least one line 82 of second sub-area. As can be seen in FIG. 11, at least two linear grating groups 76 and at least two linear aperture groups 80 are provided. The linear grating groups and the linear aperture groups are arranged in an alternating manner in a first line pitch $P_{L1}$ which is indicated with reference numeral 84 in FIG. 11. In order to provide phase gradient information for all sensor pixels, the analyzer grating is translated downwards in the vertical direction from FIG. 11a to FIG. 11b, which is once again indicated by the frame 62.

As can be seen in FIG. 11, the linear grating groups and the linear aperture groups can have the same extension in cross direction.

According to a further aspect, the linear grating groups have an extension in cross direction which is different than the extension in cross direction of the linear aperture groups. For example, the linear grating groups are smaller or larger than the linear aperture groups in the cross direction.

According to a further aspect, the linear grating groups and the linear aperture groups each comprise a different number of lines. As can be seen in FIG. 12, the linear grating group 76 comprises one line of portions 24 of first sub-area 26. The linear aperture group 80 comprises two lines 82 of portions 28 of the second sub-area 30. Accordingly, three positions P1, P2 and P3 are necessary to cover all sensor elements with the grating fields of the analyzer grating 14, which is indicated by FIGS. 12a to 12c.

According to a further aspect of the invention, the size of the pixels differs from the size of the portions of the first and/or second sub-areas of the analyzer grating 14.

For example, the pixels of the first subgroup of pixels differ from the size of the pixels of the second subgroup of pixels in at least one direction and the portions of the first sub-area are smaller than the larger one of the pixels of the first or second subgroup.

An example is shown in FIG. 13 where the underlying sensor comprises first sensor pixels 16 of the first subgroup 18 of pixels and sensor pixels 20 of the second subgroup of pixels 22, which are, as mentioned above, indicated with a dotted-line pattern. As can be seen, the sensor pixels 16 of the first subgroup 18 are twice as large in the horizontal direction. An analyzer grating 14 is provided which comprises grating fields and aperture fields in an alternating manner. As indicated in FIG. 13, the size of the grating fields, i.e. the size of the portions 24 of the first sub-area 26 is half the size in the horizontal direction as the size of the pixel 16 of the first subgroup 18. The size of the grating field 24 and the size of the pixel 20 of the second subgroup of pixels 22 are equal. To cover the whole sensor pixel 16, the analyzer grating 14 has to be translated by a translation pitch which refers to the pitch of the analyzer grating, indicated by a translation arrow 84. A sensor pixel 16 of the first subgroup 18 is indicated with a dotted-line frame 86 for illustrational purposes. As can be seen in FIG. 13a, the grating field is arranged in the right half of the dotted-line frame 86, whereas in FIG. 13b, the grating field of the analyzer grating is arranged in the left half of the dotted-line frame 86. Thus, all fields of the sensor are able to record phase grating information and density information in a first and second step.

In FIG. 13, the sensor pixels 20 of the second subgroup of pixels 22 are arranged in an alternating displaced manner with respect to the vertical direction.

FIG. 14 shows a further embodiment of the embodiment of the FIG. 13 in which the pixels 20 of the second subgroup of pixels 22 are displaced successively with respect to the vertical direction.

According to a further aspect of the invention, the pixels can be larger than the portions of the first sub-area which is indicated in FIG. 15. In order to cover the sensor pixels 16 of the first subgroup 18 with a grating field of the analyzer grating 14, two steps are necessary, which is indicated in FIG. 15a and FIG. 15b. As can be seen, the analyzer grating 14 is translated by a pitch which is adapted to the width of the portion 24 of the first sub-area 26 representing a grating structure field, e.g. the pitch is half the field's width.

According to another example (not shown), the pitch is the field's width.

In order to cover the sensor pixel 20 of the second subgroup of pixels 22, two further steps are necessary indicated with FIGS. 15c and 15d.

According to a further aspect, the pixels can be smaller than the portions of the first sub-area, which is indicated in FIG. 16.

As can be seen, in order to acquire density information with all sensor pixel areas, for example the sensor pixel 20 of the second subgroup of pixels 22, two acquisition steps are necessary, namely the first step shown in FIG. 16a and the fourth step shown in FIG. 16d. Similar, two acquisition steps are necessary for the sensor pixel 16 of the first subgroup 18, namely the second step shown in FIG. 16b and the third step shown in FIG. 16c.

According to a further aspect of the invention, it is also provided to arrange the analyzer grating 14 such that the portions 24 of the first sub-area 26 are arranged at least partially in front of the pixels 16 of the first subgroup of pixels 18 and partially in front of the sensor pixels 20 of the second subgroup of pixels 22.

According to a further aspect, a sub-part of the part covered in the third position and a sub-part of the part covered in the fourth position are covered in the fifth position.

According to a further exemplary embodiment, shown in FIG. 17, in the first and second position, the first and second sub-areas 26, 30 of the analyzer grating 14 are each arranged at least partially in front of the first subgroup of pixels 18 and at least partially in front of the second subgroup of pixels 22. In the first and second position, different first and second parts 90, 92 of the first and second subgroups of pixels 18, 22 are covered by the portions of the first sub-area of the analyzer grating respectively.

As schematically illustrated in FIG. 17, where, as an example, a sensor with sensor pixels 16 of the first subgroup of pixels 18 and sensor pixels 20 of the second subgroup of pixels 22 is shown, the sensor pixels 16, 20 are arranged in a chessboard pattern 51, which is indicated by a dotted pattern of the second pixels 20. Further, an analyzer grating 14 is shown with portions 24 of the first sub-area 26 and portions 28 of the second sub-area 30. It is noted that the portions 28 of the second sub-area 30 are shown as cut-outs in the grating structure and therefore are not further indicated for clarity reasons. The portions 24 with the grating structure are shown schematically with a line grating. The analyzer grating 14 is provided with a chessboard pattern 51 in which the portions 24 with the grating structure and the portions 28 as apertures are arranged in an alternating manner in both directions. Further, in FIG. 17a the first position P1 is shown where the analyzer grating 14 is arranged displaced in relation to the sensor 515 by half a pitch, wherein the pitch of the chessboard pattern 51 of the sensor 515 and the pitch of the chessboard pattern 51 of the grating 14 are equal. Thus, each grating field, i.e. each portion 24 of the first sub-area 26 covers both half of a first sensor pixel 16 and half of a sensor pixel 20. For example, a frame 92 indicates the first position of a particular grating field in FIG. 17a.

With reference to a particular sensor pixel, indicated by a doted-line frame 94 in the third row of the sensor pixels being the third column of sensor pixels, the grating portion 24 covers a right half of the pixel 94 which is indicated by a dotted-line frame 94a. With reference to the adjacent pixel to the right, which is indicated with reference number 96, the grating field 24 covers its left half which is indicated by a dotted-line frame 96a.

By translating the grating 14 with respect to the sensor by one pitch, indicated by the translating arrow 48, the sensor pixel 94 is now partially covered by another grating field. Thus, the grating structure now covers the left half of the sensor 94 which is indicated by a dotted-line frame 94b. With reference to the sensor pixel 96, the grating field 24 that covered the left half 96a in FIG. 17a now covers the right half which is indicated with a dotted-line frame 96b. Thus, in the second position P2 shown in FIG. 17b a different part of each pixel is covered by a grating field of the analyzer grating 14.

In a third position P3 shown in FIG. 17c the grating structure is arranged such that it covers the upper and lower halves of the sensor pixels instead of the right and left halves as shown in FIGS. 17a and 17b. The translation to the third position is indicated with a dotted-line translation arrow 98. With reference to the sensor pixel 94, a portion 24 of the first sub-area 26, i.e. a grating field of the grating 14, covers the lower half, which is indicated with a dotted-line frame 94c. With respect to sensor pixel 96, a grating field covers the upper half which is indicated with a dotted-line frame 96c.

From the third position, the grating is translated to a further position, in which further raw image data is recorded while applying coherent X-ray radiation and phase-stepping the analyzer grating. In the further position, the first and second sub-areas of the analyzer grating and the phase grating are each arranged at least partially in front of the first sub-group of pixels and at least partially in front of the second sub-group of pixels; wherein in the further position, different further parts of the first and second sub-group of pixels are covered by the portions of the first sub-area of the analyzer and phase grating respectively; which further parts partially overlap with the first and second parts respectively.

By translating the grating to a further position, for example, a fourth position P4 which is shown in FIG. 17d, which translation is indicated by translation arrow 48, the grating is moved downwards by one pitch, which is once again illustrated with the frame 92.

In the fourth position P4, with reference to sensor pixel 94, a grating field now covers the upper half which is indicated by dotted-line frame 94d. Similar, with reference to sensor pixel 96, a grating field now covers the lower half, which is indicated by a dotted-line frame 96d.

By providing the third position P3 and the fourth position P4, into which the grating is translated, two additional positions are provided in which raw image data is recorded each, while applying coherent X-ray radiation and phase stepping the analyzer grating.

Thus, so far four sets of raw image data are provided.

Further, a fifth position P5 is provided into which the grating is translated and in which fifth raw image data is recorded while applying coherent X-ray radiation and phase stepping the analyzer grating. In the fifth position P5, sub-parts of the first, second, third and fourth parts are covered by the portions of the first sub-area of the analyzer grating.

Figure 17F:
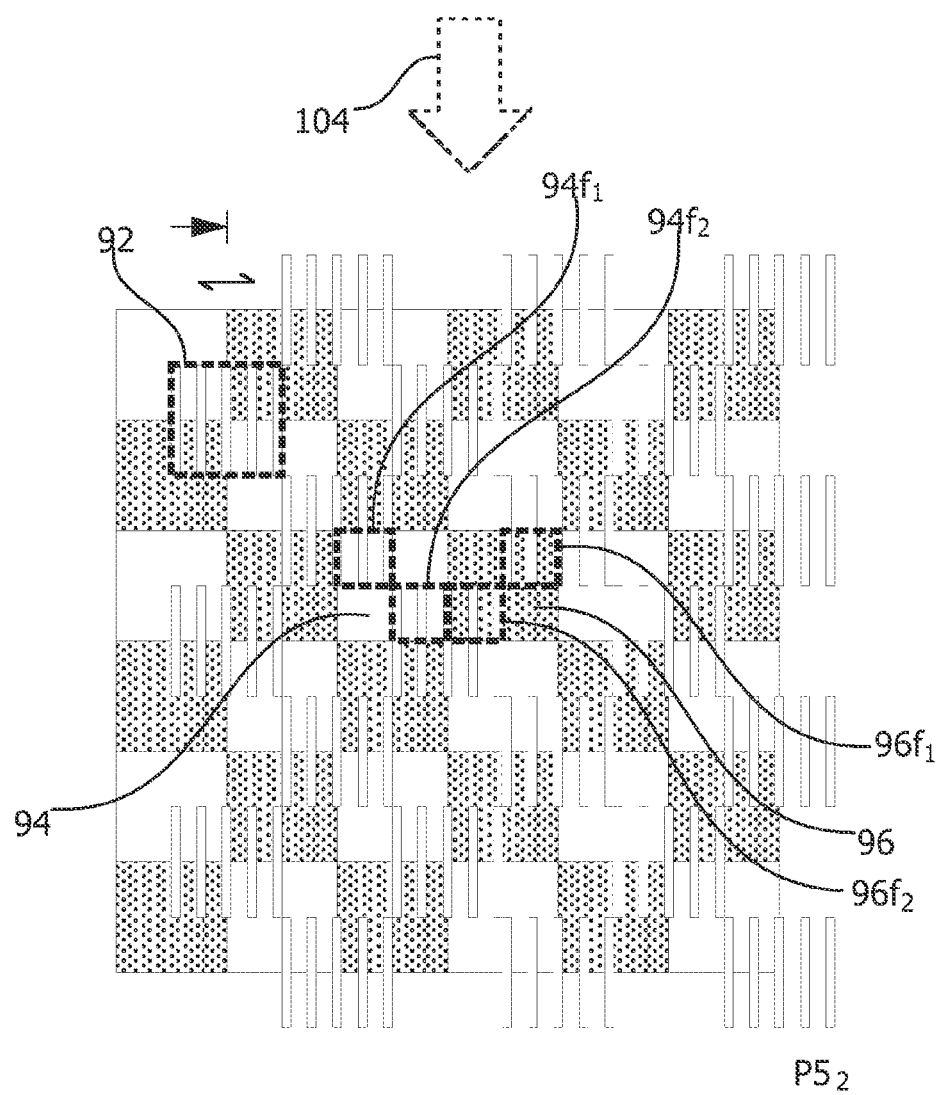

For the fifth position, two alternative possibilities are shown in FIGS. 17e and 17f.

Starting with the fourth position, it is possible to achieve a first fifth position P5$_1$ as shown in FIG. 17e by translating the analyzer grating by half a pitch, which is indicated with dotted-line translation arrow 100 and a pitch indicator arrow 102 which has half the dimension of the previous pitch arrows. As can be seen by the frame 92, each grating field of the analyzer grating 14 now covers four sensor pixels at one time, namely two first sensor pixels and two second sensor pixels.

With reference to the sensor pixel 94, the upper right quarter of the field is covered by one grating field as indicated with dotted-line frame 94e$_1$ and the lower left quarter is covered by another grating field which is indicated with a dotted-line frame 94e$_2$.

With reference to pixel 96, the upper left quart and the lower right quart are covered by a grating field which is indicated with dotted-line frames 96e$_1$ and 96e$_2$.

Thus, the frame 94e$_1$ covers both a part of the frame 94a and a part of the frame 94d.

Further, the frame 94e$_2$ now covers a part of the frame 94b and a part of the frame 94c.

Further, also with reference to pixel 96, the first, second, third and fourth parts, i.e. the frames 96a, 96b, 96c and 96d are partially covered by the portions 96e$_1$ and 96e$_2$ in a similar manner as described with reference to pixel 94.

An alternative fifth position P5$_2$ is shown in FIG. 17f. This fifth position P5$_2$ can be achieved starting from the third position by translating the analyzer grating 14 by half a pitch to the right, which is indicated with a dotted-line translation arrow 104 and a half pitch arrow 106.

As can be seen, in the fifth position P5$_2$, subparts of the first, second, third and fourth parts are covered by the portions of the grating fields of the analyzer grating 14. Since the parts of the sensor pixels 94 and 96 are covered in so to speak a mirrored manner, i.e. instead of the upper right quart and the lower left quart, in pixel 94, the upper left and the lower right quart are covered, and similar applies to pixel 96, a repetition of the above-described aspects is not necessary at this point.

According to a further aspect, from the third position, the analyzer grating is translated in relation to the sensor from the third position to the fourth position with a second translation pitch $P_{T2}$, which second translation direction is perpendicular to the first translation direction.

For example, this is indicated in FIG. 17c with a pitch arrow 108c pointing downwards whereas in FIGS. 17a and 17b the translation is indicated with pitch arrows 108a and 108b leading to the right.

In FIG. 17, the pitch $P_{T2}$ has equal length compared with the pitch applied in the first translation step from P1 to P2. Of course, the second translation pitch $P_{T2}$ can also have a different value.

With reference to FIG. 17, it is possible to achieve a spatial resolution improvement by a factor of 2 in either the horizontal direction, which is shown in FIGS. 17a and 17b, or in the vertical direction which is shown in the FIGS. 17c and 17d. As explained above, for each of the translational positions of the analyzer grating, an entire phase stepping loop has to be performed. By only performing the steps of FIGS. 17a and 17b or the steps of FIG. 17c and FIG. 17d, the resolution can be improved either in the vertical or in the horizontal direction but not in both directions at the same time.

An embodiment for which this is possible, as explained above, is illustrated by FIG. 17e or 17f In other words, if the four phase stepping procedures of FIGS. 17a to 17d are supported by either of the two stepping cycles shown in FIGS. 17e and 17f, the spatial resolution can be improved in the vertical and the horizontal direction simultaneously. Thus, from the five resulting phases, the phase gradient in each quarter of the indicated pixel 95 in FIGS. 17a to 17d in combination with either 17e or 17f can be computed.

According to a further exemplary embodiment, the first and/or second diffraction gratings are each adapted to be phase-stepped in relation to one period of the diffraction grating structure with the first grating pitch $P_{G1}$ in an acute angle α to the grating structure of the first and/or second diffraction grating.

According to a further exemplary embodiment, the analyzer grating is adapted to be phase-stepped in relation to one period of the analyzer grating structure with the first grating pitch $P_{G1}$ in an acute angle α to the grating structure of the analyzer grating. For example, the acute angle is smaller than 90°.

According to a further exemplary embodiment, the phase grating is also adapted to be phase-stepped in relation to one period of the analyzer grating structure with the first grating pitch $P_{G1}$ in an acute angle α to the grating structure of the analyzer grating. For example, the acute angel is smaller than 90°.

According to a further aspect, from the third position, the analyzer grating is translated in relation to the sensor from the third position to the fourth position with a second translation pitch $P_{T2}$; which second translation direction is perpendicular to the first translation direction (not shown).

Figure 18D:
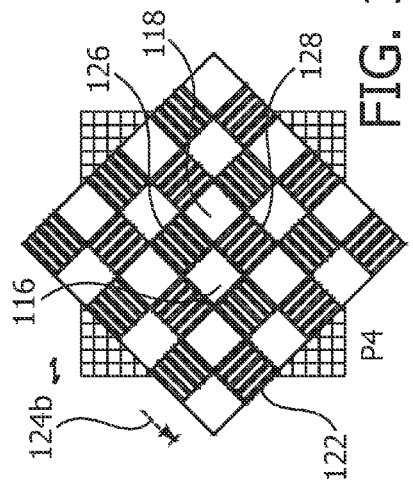
Figure 19D:
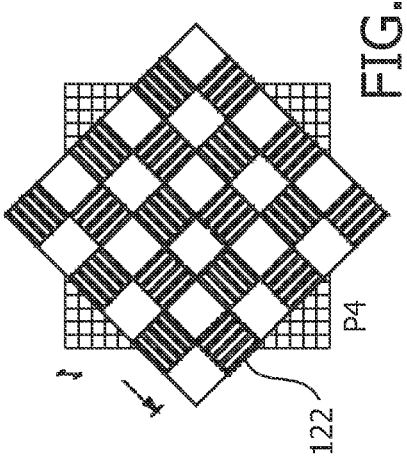

According to a further exemplary embodiment, an example of which is shown in FIGS. 18 and 19, where, for illustrative purposes, the analyzer grating 14 together with the detector 12 has been rotated by an angle of 45° which is indicated with reference numeral 109. As indicated by a shifting double arrow 113, the analyzer grating is phase-stepped in a horizontal direction, i.e. to the left and right.

It must be noted that terms as "right", "left", "upwards" or downwards" as well as "horizontal" and "vertical" relate to the page on which the figures are presented when looking at the pages in such a manner that the letters and numbers can be read, i.e. in most of the cases the figure pages are regarded in a landscape orientation.

The X-ray radiation applied to the gratings has coherence in two directions.

For example, a source grating with two grating directions is used, e.g. a grid-like source grating or source grating with a grid or raster structure.

According to another example, a microfocus tube is provided.

According to a further example, for the coherent X-ray radiation, a plurality of nano-tubes is provided in order to generate a respective plurality of X-ray beams.

According to the embodiment shown in FIGS. 18 and 19, a radiation is applied which has a high transversal coherence in two directions, which is symbolically indicated by a grid with lines, for which the reference numeral 114 is used.

It is noted that the grid 114 is shown such that the corners of the square-like grid patterns extend beyond the grid, because the grid 90 only indicates the rotated orientation of coherence and grating structure and not the actual sizes. Of course, the gratings can be fully radiated with the radiation with two coherence directions, i.e. the detector and the gratings are radiated over their whole area.

According to another aspect, a radiation is provided that covers the gratings and/or the detector only partially.

According to a further embodiment, although not shown, x-ray beams with transverse coherence in only one of the directions shown in the figure, is provided, e.g. by providing one or several line sources.

With reference to a selected pixel of the sensor, which is indicated with reference numeral 116, by phase stepping the grating to the left and right, phase gradient information perpendicular to the particular grating sub-structure arranged in front of the pixel 116 can be acquired since the phase stepping direction is rotated by the angle of 45° but the resulting projection can be computed such that the information is achieved. When regarding the neighbouring pixel to the right which is indicated with reference numeral 118, by phase stepping the grating in a horizontal direction which is in an angle to the direction of highest transverse coherence 114, for this particular pixel, phase gradient information perpendicular to the particular sub-grating arranged in front of the pixel 118 is achieved. Next, i.e. after this first phase-stepped acquisition, the grating is translated by one pixel as indicated with pitch arrows 120a indicating that the grating is going to be translated and the arrow 120b indicating that the grating has been translated. However, a frame 122 is provided indicating the same grating field throughout the translating steps. Thus, the analyzer grating is translated from the first position P1 in FIG. 18a to a second position P2 in FIG. 18b. As can be seen, in front of the pixels 116 and 118, now there is no sub-grating field arranged but the aperture fields of the analyzer grating. Thus, with reference to these particular pixels, density information is now acquired.

Figure 18C:
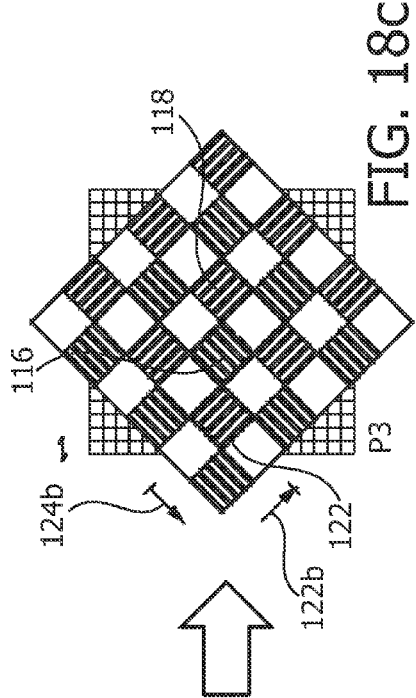
Figure 19C:
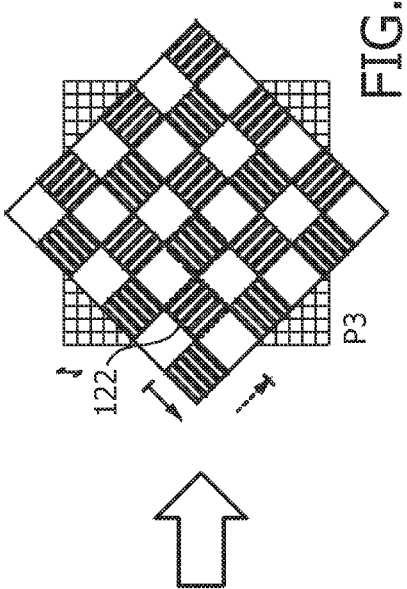

In a next translating step, i.e. a second translating step, indicated with translating arrows 122a in FIG. 18b and 122b in FIG. 18c, the analyzer grating is once again stepped by one pitch in this case to the right downwards direction. As can be seen by the illustration in FIG. 18c, in front of the pixel 116, a field of the analyzer grating is arranged in front of this pixel with a grating structure oriented in a perpendicular direction compared with the grating field arranged in front of this pixel in position P1 in FIG. 18a. Thus, a third position is provided in which the two sensor pixels 116 and 118 are each covered with a grating field of the analyzer grating 14.

According to a further aspect of the invention, the grating structure of the first sub-area comprises at least one first grating field 110 with a first grating orientation $G_{O1}$ and at least one second grating field 112 with a second grating orientation $G_{O2}$, wherein the grating orientation $G_{O1}$ of the first grating field is arranged in a first orientation and wherein the grating orientation $G_{O2}$ of the second grating field is arranged in a second orientation which is transverse to the first orientation.

In FIG. 18c, the first and second pixels 116, 118 are now covered with a grating structure which has a direction perpendicular to that grating orientation of the particular grating field in FIG. 18a. Hence, phase gradient information in a different direction is now acquired for the pixels 116 and 118. Then, in a third translation step, as indicated by translation arrow 124a in FIG. 18c and translation arrow 124b in FIG. 18d, a fourth position P4 is provided in which once again, the pixels 116 and 118 are not covered by a grating structure but are provided with an aperture field of the analyzer grating. Thus, in this position, for the two pixels density information is recorded. However, if looking at the adjacent pixels, indicated with reference numerals 126 and 128, for these two pixels, phase gradient information is recorded in the fourth position, as is also the case in the second position. Of course, the phase gradient information in the second position and in the fourth position has a different direction since the gratings of the grating field have different orientations in these two positions.

In FIGS. 19a, 19b, 19c and 19d, a second possibility for a phase stepping direction is shown, as indicated with a phase stepping arrow 130 which is oriented in the vertical direction, i.e. parallel to one of the two coherence directions of the source. However, since the grating structures are arranged in an angle towards this phase stepping direction 130, the same phase gradient information can be achieved in the four positions compared to the illustrations of FIG. 18a to 18d. Thus, these steps are not further described but indicated with similar reference numerals.

The demands on transverse coherence are increased by a factor of square root of 2 with respect to a conventional setup in order to compensate for the increase in the projected pitch onto the vertical or horizontal directions. The advantages are that the phase stepping in two perpendicular directions can be performed only by a translation of gratings perpendicular or parallel to the orientations of the source grating. As mentioned above, the angle of rotation is shown to be 45°, which is a preferred angle.

By providing a rotated grating in relation to the direction of the two coherences of the source, it is possible to achieve gradient information for two different directions, by providing an analyzer grating with portions of the first sub-area 26 having different directions. However, in order to provide phase gradient information for all pixels, additional steps are necessary.

According to a further exemplary embodiment, not shown, the grating structure of FIGS. 18 and 19 can be combined with synchrotron radiation or microfocus tubes, i.e. a radiation which has coherence in two directions, wherein the grating needs not to be rotated.

According to a further exemplary embodiment not shown, the phase stepping direction comprises an angle of 30-60° to the direction of the grating structure.

For example, an angle clearly distinguishable from 45°, e.g. 30°, is applied for the phase-stepping direction. By stepping at a different angle than 45°; it is possible to distinguish between the phase gradient over the two parts of the pixel by the frequency of the modulation during phase stepping. This allow for improved image information acquisition.

According to an exemplary embodiment, the diffraction grating is an analyzer grating for X-ray differential phase-contrast imaging.

According to a further exemplary embodiment, the diffraction grating is a phase grating for X-ray differential phase-contrast imaging.

According to a further exemplary embodiment, two diffraction gratings are combined as a phase grating and an analyzer grating in order to provide an interferometer, also referred to as Talbot-Lau-Interferometer for X-ray differential phase-contrast imaging.

It is noted that the term "diffraction" grating is also applied to an analyzer grating, although the diffraction effect of this grating is not detected, since the detector is arranged close to the analyzer grating. However, since diffraction is actually induced by such grating, the term diffraction grating is suitable.

It is further noted that the purpose of a phase grating is to induce diffraction and thus detectable interference patterns. Thus, the phase grating needs not to be X-ray absorbing in order to change the phase of the X-ray radiation. However, this can also be achieved by an absorbing grating as defined in the claims.

It is further explicitly noted that, according to a further exemplary embodiment (not shown), the absorbing characteristic of the diffraction grating can be omitted with respect to the phase grating. According to the invention, sub-areas are provided that induce interference, i.e. that provide diffraction, and subareas where no diffraction occurs.

Figure 20:
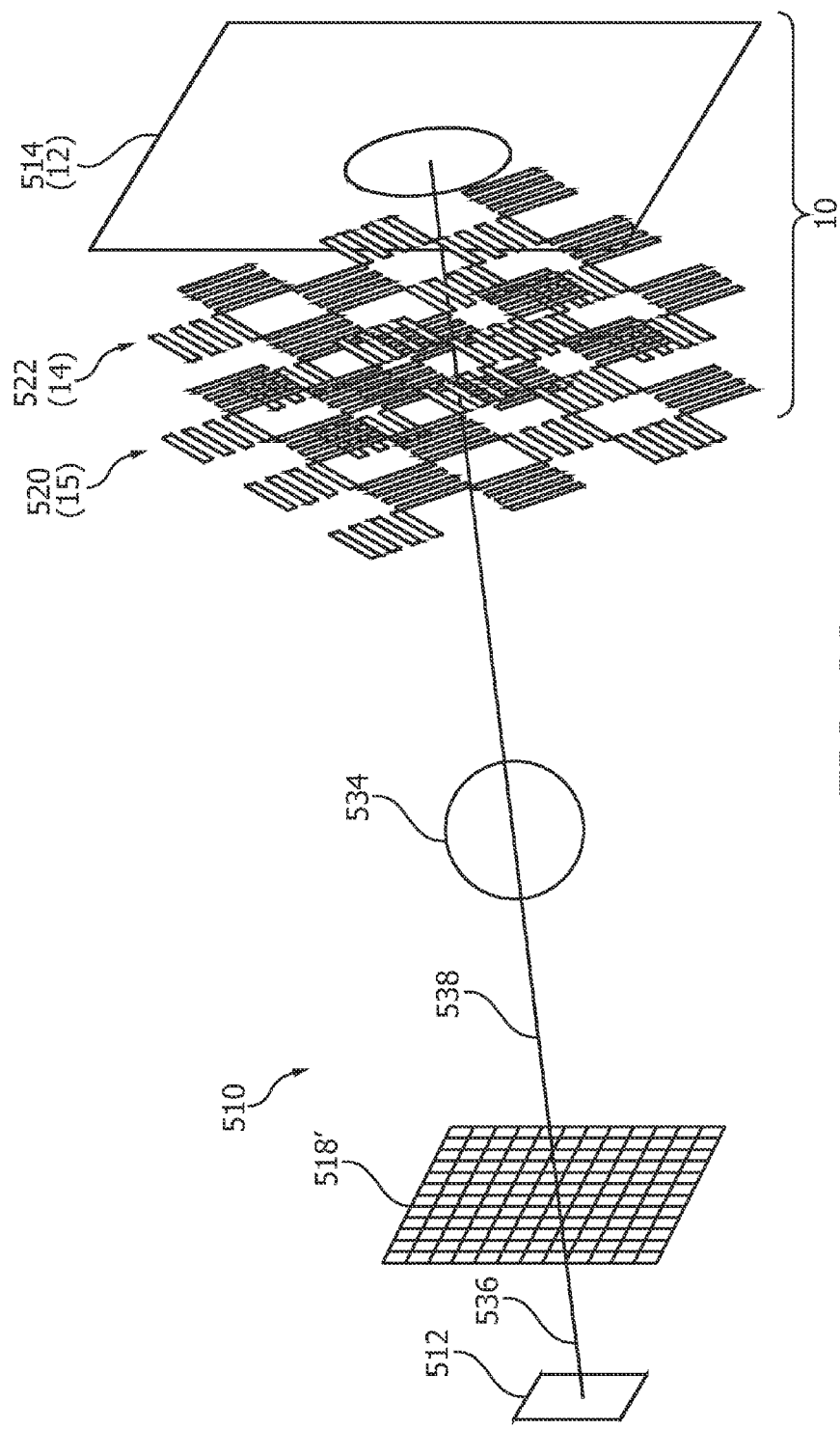
FIG. 20 schematically shows a further exemplary embodiment of an X-ray image acquisition device for generating phase-contrast images according to the invention.

A detector arrangement 10 with rotated phase and analyzer gratings 15, 14 (also indicated with reference numerals 520, 522) is shown in FIG. 20. As a source grating 518', a grid-like structure is shown indicating the transversal coherence in two directions as described above.

Of course, instead of the source grating 518' and the source 512 provided as a conventional X-ray source, a microfocus tube or microfocus tube arrangement, e.g. an array, can be provided.

According to a further exemplary embodiment (not shown), instead of the grid-like source grating, a linear source grating resulting in coherence in only one direction is provided.

Figure 21:
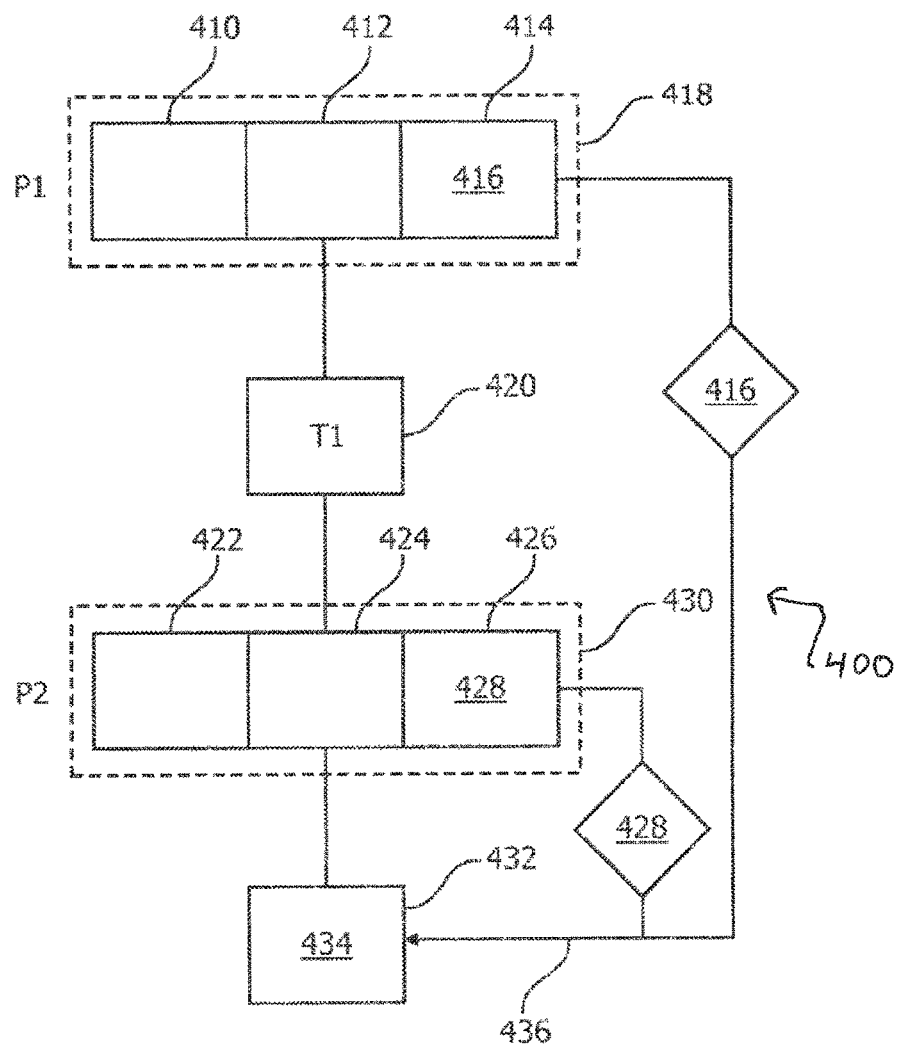
FIG. 21 shows basic method steps of an exemplary embodiment of the invention.

According to a further exemplary embodiment, a method 400 for differential phase-contrast imaging is provided, which is explained with reference to FIG. 21. The method 400 comprises the following steps: In a first position P1, in a first application step 410, coherent X-ray radiation is applied to a phase grating and an analyzer grating in the first position P1. The phase grating and the analyzer grating each comprise at least one grating part and an at least an aperture part. Next, in a phase stepping step 412, the analyzer grating is phase-stepped and in a further recording step 414, first raw image data 416 is recorded with a sensor with at least two parts, wherein a first and a second part are recording phase-contrast image information and density information. The three steps 410, 412 and 414 are performed at the same time which is indicated with a dotted-line rectangular 418 surrounding the three steps. Further, in a translation step T1, indicated with reference numeral 420, the phase grating and the analyzer grating are translated to a second position P2. Then, in a second application step 422, coherent X-ray radiation is applied to the phase grating and the analyzer grating in the second position P2. During the application, in a second phase stepping step 424, the analyzer grating is phase-stepped. At the same time, in a second recording step 426, second raw image data 428 is recorded with a sensor with at least two parts, wherein in the first and second part are recording density information and phase-contrast image information. The simultaneous performing of the three steps 422, 424 and 426 is indicated with a second dotted-line rectangular 430. In a provision step 432, the recorded first and second raw image data 416, 428 are provided as raw image data 434. The combination of the first raw image data 416 and the second raw image data 428 is indicated with an arrow 436.

The application step 410 is also referred to as step a1), the phase stepping step 412 as step a2), the recording step 414 as step a3), the translating step 420 as step b), the second application step 422 as step c1), the second phase stepping step 422 as step c2), the second recording step 426 as step c3) and the provision step 432 as step d).

According to a further exemplary embodiment (not further shown), step a2) comprises phase-stepping the analyzer grating in a first position transversely in relation to one period of the analyzer grating structure with the first grating pitch $P_{G1}$. Further, step c2) comprises phase-stepping the analyzer grating in the second position transversely in relation to one period of the analyzer grating structure with the first grating pitch $P_{G1}$.

According to a further aspect, in the first position, the first sub-areas of the phase grating and the analyzer grating are arranged in front of the first sub-group of pixels and the second sub-areas are arranged in front of the second sub-group of pixels. Further, the first sub-group is recording phase contrast image information and the second sub-group is recording density information.

According to a further aspect, in the second position, the first sub-areas of the phase grating and the analyzer grating are arranged in front of the second sub-group of pixels and the second sub-areas are arranged in front of the first sub-group of pixels. The first sub-group is recording density information and the second sub-group is recording phase contrast image information.

According to a further aspect, as already mentioned above, in the first position the first part of the detector is recording phase-contrast image information, and the second part is recording density information. In the second position, the first part is recording density information and the second part is recording phase-contrast image information.

Figure 22:
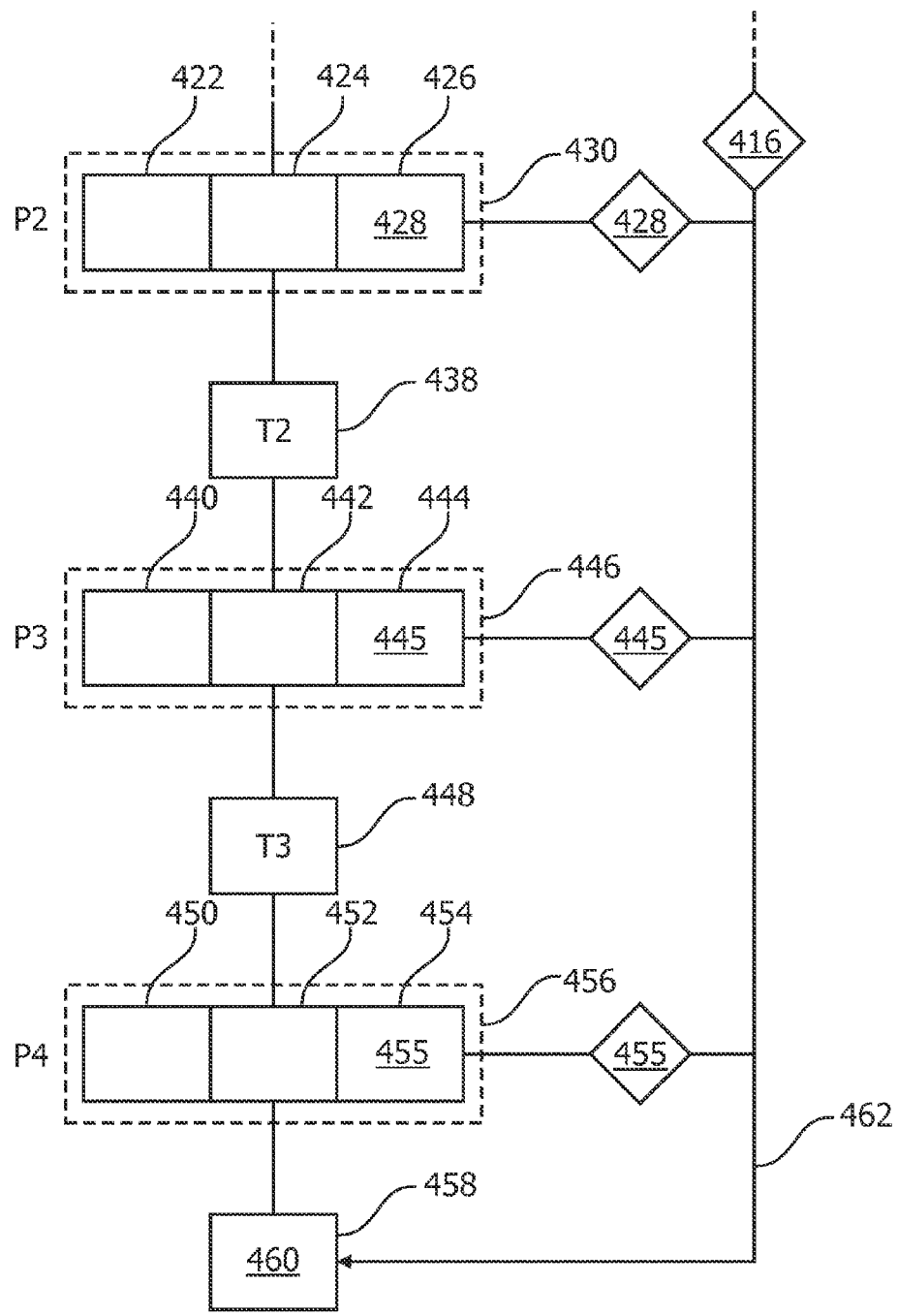
FIG. 22 shows a further exemplary embodiment of a method according to the invention.

In FIG. 22, a further exemplary embodiment of the method is schematically illustrated. Following the second acquisition step indicated with the second dotted-line rectangular 430, a second translation step T2, indicated with reference numeral 438, is provided in which the phase grating and the analyzer grating are translated to a third position P3. In the third position, a third application step 440, a third phase stepping step 442 and a third recording step 444 are provided in a similar fashion as the respective steps described above with reference to FIG. 21. Once again, these steps, providing third image data 445, are performed simultaneously which is indicated with a third dotted-line rectangular 446.

Further, a third translation step T3, indicated with reference numeral 448, is provided in which the phase grating and the analyzer grating are translated to a fourth position P4. In this fourth position, a fourth application step 450, a fourth phase stepping step 452 and a fourth recording step 454, providing fourth image data 455, are provided simultaneously, which is indicated by a fourth rectangular in a dotted-line, with reference numeral 456. Thus, first, second, third and fourth raw image data are provided which in a providing step 458 are provided as raw image data 460, wherein the combination and computational steps are indicated with arrow 462.

One of the advantages of the inventive diffraction grating structures is that phase gradient information is acquired for the complete grating area as well as density information for the whole area. Compared to a conventional first step with a conventional grating and a second step as X-ray image without any grating, no grating removal is necessary which saves time and constructional space and also means a great relief for the clinical staff, since the steps can be performed automatically.

Further, for example when providing a chessboard pattern, in the first step, for every second pixel, phase gradient information is acquired, and for every other pixel, density information is acquired. In the second step this is vice versa. However, also from each "grated" pixel, density information can be retrieved by computing the average density from the phase stepping results.

By modifying the grating structure such that not the entire diffraction grating is uniformly covered with equidistant trenches of adsorbing material, for example gold, several embodiments are possible, some of them are described above. For example, the gold trenches will in the simple case cover only the squares of one colour of the shown chessboard pattern formed by square pixels of the detector. If one complete phase stepping cycle is performed with the gold trenches aligned over the white squares, the phase gradient of the X-ray wave field can be determined there as usual whereas the interference fringes over the black squares remain unresolved. After that, the analyzer grating and the phase grating can be translated by one pixel size in either of the two dimensions along the X-ray detector to align the gold filled trenches with the black squares of the chessboard. The phase stepping can now be repeated there and the phase grating is thus measured over the entire detector. Thus, a beneficial trade off between dose efficiency and X-ray power utilized in the generation of phase-contrast is achieved.

When the gold chessboard trench pattern is offset from either the white or the black squares by one half of the pixel width or height, a phase stepping at that position will improve the spatial sampling of the phase gradient by a factor of 2. To complete the sampling of the phase gradient, the phase stepping has to be repeated with the analyzer grating and the phase grating shifted by a full pixel pitch in the same direction in which the half pitch offset was realized. To obtain an isotropic resolution improvement, according to one aspect, at least two more phase stepping procedures are required with offsets perpendicular to the offsets realized before.

Thus, the described imaging sequence allows for an improvement of the spatial resolution of the phase gradient by a factor of 2 in both directions with improved dose efficiency by a factor of 2 but at the expense of a 2-fold reduction in phase sensitivity. However, in case the focal spot size is the limiting factor of spatial resolution, the grating-structure needs a respective adaption.

Figure 23:
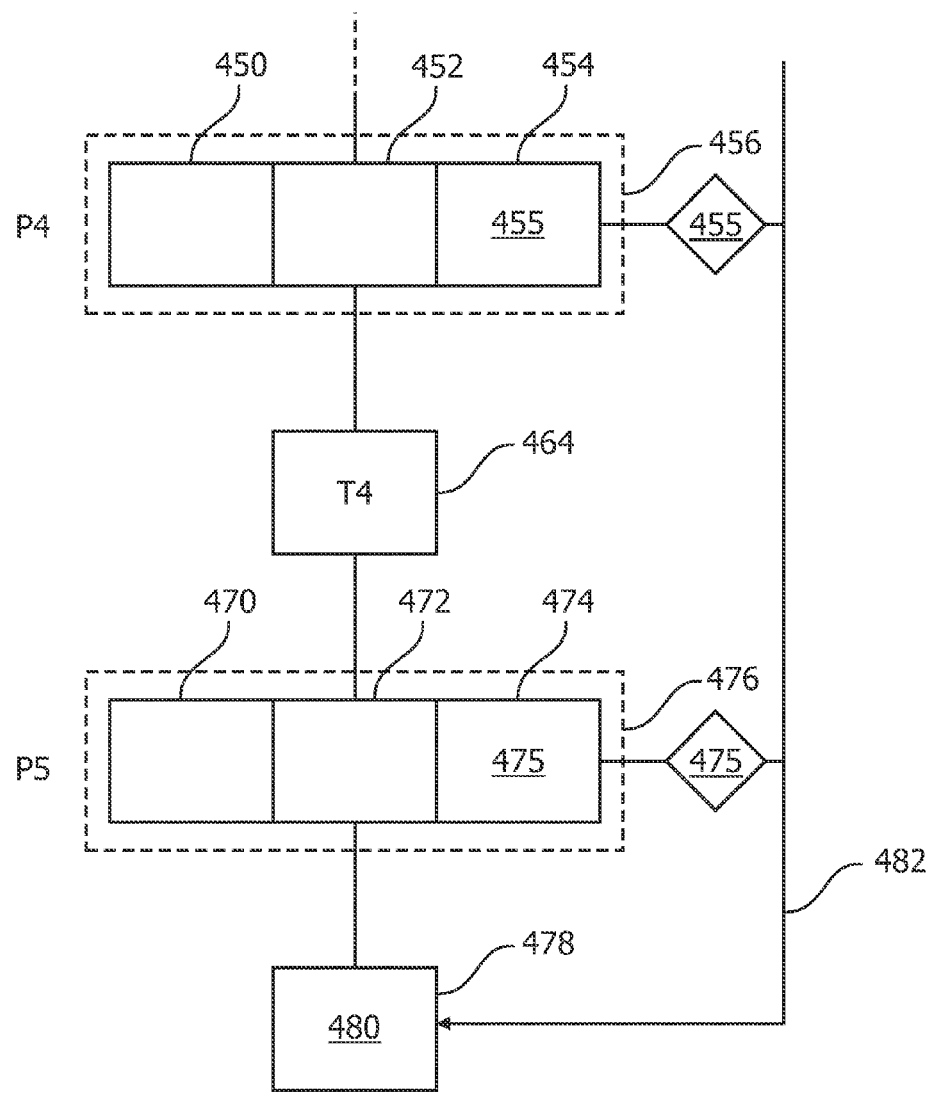
FIG. 23 shows a further exemplary embodiment of a method according to the invention.

According to a further exemplary embodiment, shown in FIG. 23, following the fourth acquisition in position P4, a fourth translation step T4, indicated with reference numeral 464, is performed in which the grating is translated into a fifth position P5 in which fifth raw image data 475 is recorded 474 while applying 470 coherent X-ray radiation and phase-stepping 472 the analyzer grating. In the fifth position, sub-parts $94e_1$, $94e_2$, $96e_1$, $96e_2$ in FIG. 17e, or $94f_1$, $94f_2$, $96f_1$, $96f_2$ in FIG. 17f, of the first, second, third and fourth parts are covered by the portions of the first sub-area of the analyzer grating and the phase grating. The X-ray-applying, recording and phase-stepping steps are provided at the same time which is indicated with a dotted-line rectangular 476. Then, the recorded first, second, third, fourth and fifth raw image datasets are provided 478 as raw image data 480. Of course, computational steps are provided in order to provide the raw image data 480; the combination and computational steps are indicated with arrow 482.

According to a further exemplary embodiment, shown also in FIG. 17, the fourth acquisition step is not applied, but the fifth acquisition step is provided instead. Thus, it is also possible to achieve enhanced image data for further processing due to the following computational steps. For example, in FIG. 17a, in position P1, for pixel 96, a+c=m1 is measured; in position P2, b+d=m2 is measured and in position P3 a+b=m3.

In position P4, c+d=m4 would be measured. The matrix thus obtained for this system of linear equations would be singular. As mentioned above, if measurement P4 is omitted and position P5 is measured instead, leading to the sequence P1, P2, P3, P5, the following equation applies:

$$A \cdot x = m \text{ with}$$

$$\begin{pmatrix} 1 & 0 & 1 & 0 \\ 0 & 1 & 0 & 1 \\ 1 & 1 & 0 & 0 \\ 1 & 0 & 0 & 1 \end{pmatrix} \begin{pmatrix} x_a \\ x_b \\ x_c \\ x_d \end{pmatrix} = \begin{pmatrix} m_1 \\ m_2 \\ m_3 \\ m_4 \end{pmatrix}$$

According to a further exemplary embodiment, instead of the fourth and fifth position, one of the fifth positions ($P5_1$; $P5_2$) is provided into which the analyzer grating and the phase grating are translated (464) and in which fifth raw image data is recorded (474) while applying (470) coherent X-ray radiation and phase-stepping (472) the analyzer grating; wherein in the fifth position, sub-parts ($94e_1$, $94e_2$, $96e_1$, $96e_2$; $94f_1$, $94f_2$, $96f_1$, $96f_2$) of the first, second, third and fourth parts are covered by the portions of the first sub-areas of the analyzer grating and the phase grating.

The invention claimed is:

1. A phase grating configured for X-ray differential phase-contrast imaging, comprising:
   a first sub-area comprising at least one portion; and,
   alongside said first sub-area, a second sub-area comprising at least one portion;
   wherein the first sub-area comprises a grating structure with a plurality of bars, and a plurality of gaps, arranged periodically with a first grating pitch $P_{G1}$;
   wherein the plurality of bars are arranged so as to change at least one of phase and amplitude of an X-ray radiation and wherein the plurality of gaps are X-ray transparent;
   wherein said second sub-area is X-ray transparent;
   wherein said at least one portion of the second sub-area provides an X-ray transparent aperture in said phase grating configured for X-ray differential phase-contrast imaging; and
   wherein multiple portions from among collectively said at least one portion of said first sub-area and said at least one portion of said second sub-area are arranged, in at least one direction, in a pattern characterizable as alternating by sub-area.

2. The phase grating according to claim 1, wherein said phase grating has an area comprising said first sub-area and said second sub-area, ones from among said portions of collectively said first sub-area and said second sub-area being arranged across said area in a chess-board pattern, from a standpoint of portion-wise belonging to said first sub-area versus portion-wise belonging to said second sub-area.

3. The phase grating of claim 2, wherein said portions of collectively said first sub-area and said second sub-area are arranged across said area in said chessboard pattern.

4. The phase grating of claim 1, wherein said at least one portion of said first sub-area comprises multiple portions of said first sub-area; wherein said at least one portion of said second sub-area comprises multiple portions of said second sub-area; wherein, for at least one of said first sub-area and said second sub-area, said multiple portions are arranged adjacent as correspondingly first subsets and/or second subsets; and wherein the first subsets, the second subsets, or both said first subsets and said second subsets are, respectively in at least one direction, arranged across an area of said phase grating in direction-wise correspondingly a first subset-repetition pitch $P_{SR1}$ and/or a second subset-repetition pitch $P_{SR2}$.

5. The phase grating of claim 1, wherein said at least one portion of said first sub-area comprises at least two linear grating groups, each of said at least two linear grating groups comprising one line of a plurality of portions of said first sub-area arranged linearly; wherein said at least one portion of said second sub-area comprises at least two linear aperture groups, each of said at least two linear aperture groups comprising one line of a plurality of portions of said second sub-area arranged linearly; and wherein said at least two linear grating groups and said at least two linear aperture groups are arranged in an alternating manner in a first line pitch $P_{L1}$.

6. The phase grating of claim 1,
   wherein said alternating alternates between said first sub-area and said second sub-area; and
   wherein said alternating occurs in a direction from among said at least one direction.

7. The phase grating of claim 6,
   wherein said first sub-area and said second sub-area have respective surfaces having corresponding areas; and
   wherein said phase grating comprises said first sub-area and said second sub-area, said first sub-area being disposed non-overlapping with said second sub-area so as to form a surface having an area characterizable as a sum of said corresponding areas.

8. The phase grating of claim 6, a portion from among said multiple portions of said first sub-area being arranged in a side-by-side arrangement in said phase grating with a portion from among said multiple portions of said second sub-area, wherein said side-by-side arrangement is in a direction across said phase grating.

9. The phase grating of claim 1, wherein said at least one portion of a first sub-area and said at least one portion of a second sub-area are, in said at least one direction, arranged in said pattern characterizable as alternating by sub-area.

10. A diffraction grating configured for X-ray differential phase-contrast imaging, said diffraction grating having an area and comprising:
    a first sub-area comprising multiple portions; and
    a second sub-area comprising multiple portions;
    wherein said first sub-area comprises a grating structure with a plurality of bars, and a plurality of gaps, the plurality of bars being arranged interleavingly with the plurality of gaps and with a first grating pitch $P_{G1}$;
    wherein the plurality of bars are arranged so as to change at least one of phase and amplitude of an X-ray radiation;
    wherein said plurality of gaps being X-ray transparent;
    wherein said second sub-area is X-ray transparent;
    wherein said multiple portions of said second sub-area provide, both collectively and individually, an X-ray transparent aperture in said diffraction grating configured for X-ray differential phase-contrast imaging;
    wherein, for a group consisting collectively of said multiple portions of said first sub-area and said multiple portions of said second sub-area, ones of the portions that make up said group are, in a direction, arranged, from a standpoint of portion-wise belonging to said first sub-area versus portion-wise belonging to said second sub-area, alternatingly, such that, during one image acquisition step, both phase-contrast image information and density information are recordable,
    wherein, for at least one of said first sub-area and said second sub-area, said multiple portions are arranged adjacent as correspondingly first subsets and/or second subsets; and
    wherein correspondingly said first subsets and/or said second subsets are arranged, in respectively at least one direction, across said area in direction-wise correspondingly a first subset-repetition pitch $P_{SR1}$ and/or a second subset-repetition pitch $R_{SR2}$.

11. A diffraction grating configured for X-ray differential phase-contrast imaging, comprising:
    a first sub-area comprising multiple portions; and
    a second sub-area comprising multiple portions;
    wherein said first sub-area comprises a grating structure with a plurality of bars and a plurality of gaps, the plurality of bars and the plurality of gaps being arranged periodically with a first grating pitch $P_{G1}$;
    wherein the plurality of bars are arranged so as to change at least one of phase and amplitude of an X-ray radiation;
    wherein the plurality of gaps are X-ray transparent;
    wherein said second sub-area is X-ray transparent;
    wherein said multiple portions of said second sub-area provide an X-ray transparent aperture in said diffraction grating configured for X-ray differential phase-contrast imaging;
    wherein, for a group consisting collectively of said multiple portions of said first sub-area and said multiple portions of said second sub-area, the portions are, in a direction, arranged, from a standpoint of portion-wise belonging to said first sub-area versus portion-wise belonging to said second sub-area, alternatingly, such that, during one image acquisition step, both phase-contrast image information and density information are recordable;
    wherein among said multiple portions of said first sub-area are at least two linear grating groups, each of said at least two linear grating groups comprising a respective plurality of said multiple portions of said first sub-area, the portions of said respective plurality being arranged linearly;
    wherein among said multiple portions of said second sub-area are at least two linear aperture groups, each of said at least two linear aperture groups comprising a respective plurality of said multiple portions of said second sub-area, the portions of said respective plurality being arranged linearly; and
    wherein said at least two linear grating groups and said at least two linear aperture groups are arranged in an alternating manner in a first line pitch $P_{L1}$.

12. An X-ray image acquisition device configured for X-ray differential phase-contrast imaging, said X-ray image acquisition device including:
    a diffraction grating configured for X-ray differential phase-contrast imaging comprising:
    a first sub-area comprising at least one portion; and,
    laterally adjacent to said first sub-area, a second sub-area comprising at least one portion;
    wherein said first sub-area comprises a grating structure with a plurality of bars and a plurality of gaps, wherein the plurality of bars and the plurality of gaps are arranged periodically with a first grating pitch $P_{G1}$;
    wherein said plurality of bars are arranged so as to change at least one of phase and amplitude of an X-ray radiation;
    wherein said plurality of gaps are X-ray transparent;
    wherein said second sub-area is X-ray transparent;
    wherein said at least one portion of said second sub-area provides an X-ray transparent aperture in said diffraction grating;
    wherein, from among collectively a) and b), wherein a) and b) are defined as: a) said at least one portion of said first sub-area; b) said at least one portion of said second sub-area, ones of the portions are, in a direction, arranged, from a standpoint of portion-wise belonging to said first sub-area versus portion-wise belonging to said second sub-area, alternatingly;

said X-ray image acquisition device being configured for recording, during one image acquisition step, both phase-contrast image information, conveyed via said X-ray radiation that has propagated through a portion from among said at least one portion of said first sub-area, and density information, conveyed via said X-ray radiation that has propagated through a portion from among said at least one portion of said second sub-area.

13. The X-ray image acquisition device of claim 12, wherein a portion from among said at least one portion of said first sub-area is arranged in a side-by-side arrangement in said diffraction grating with a portion from among said at least one portion of said second sub-area; and wherein said side-by-side arrangement is in a direction across said diffraction grating.

14. The X-ray image acquisition device of claim 13, wherein the portions arranged in said side-by-side arrangement are from among the at least one portion of said first sub-area and said at least one portion of said second sub-area that are arranged alternatingly.

15. The X-ray image acquisition device of claim 13, wherein the two portions arranged in said side-by-side arrangement are from among the at least one portion of said first sub-area and said at least one portion of said second sub-area that are arranged alternatingly.

16. The X-ray image acquisition device of claim 12, wherein said first sub-area and said second sub-area have respective surfaces having corresponding areas; and wherein said diffraction grating comprises said first sub-area and said second sub-area, said first sub-area being disposed non-overlapping with said second sub-area so as to form a surface having an area characterizable as a sum of said corresponding areas.

17. The X-ray image acquisition device of claim 12, wherein a first portion from among said ones that belong to said first sub-area is specialized for said recording, during said one image acquisition step, of said phase-contrast image information, and a second portion from among said ones that belong to said second sub-area is specialized for said recording, during said one image acquisition step, of said density information, wherein said first portion is different from said second portion.

18. The X-ray image acquisition device of claim 12, wherein said ones of the portions that are, in a direction, arranged, from a standpoint of portion-wise belonging to said first sub-area versus portion-wise belonging to said second sub-area, alternatingly are in an alternating arrangement;
wherein:
A) a portion from among those in said alternating arrangement that belong to said first sub-area is specialized for said recording, during said one image acquisition step, of said phase-contrast image information; and
B) a portion from among those in said alternating arrangement that belong to said second sub-area is specialized for said recording, during said one image acquisition step, of said density information; and
wherein the portion specialized for said recording, during said one image acquisition step, of said phase-contrast image information is different from the portion specialized for said recording, during said one image acquisition step, of said density information.

19. The X-ray image acquisition device of claim 12, configured such that said diffraction grating is one of a phase grating and an analyzer grating.

20. The X-ray image acquisition device of claim 12, wherein said at least one portion of said first sub-area amounts to multiple portions of said first sub-area, and said at least one portion of said second sub-area amounts to multiple portions of said second sub-area.

21. The X-ray image acquisition device of claim 20, wherein: said diffraction grating has an area comprising both said first sub-area and said second sub-area; for at least one of said first sub-area and said second sub-area, said multiple portions are arranged adjacent as correspondingly first subsets and/or second subsets; and correspondingly said first subsets and/or said second subsets are arranged, in respectively at least one direction, across said area in direction-wise correspondingly a first subset-repetition pitch $P_{SR1}$ and/or a second subset-repetition pitch $P_{SR2}$.

22. The X-ray image acquisition device of claim 12, further comprising an X-ray detector that includes an X-ray sensor, said X-ray sensor including at least two distinct parts,
wherein said recording, during said one image acquisition step, of phase-contrast image information, conveyed via said X-ray radiation that has propagated through a portion from among said at least one portion of said first sub-area utilizes X-rays received by one of said at least two distinct parts; and
wherein said recording, during said one image acquisition step, of density information, conveyed via said X-ray radiation that has propagated through a portion from among said at least one portion of said second sub-area utilizes X-rays received by a different one of said at least two distinct parts.

23. The X-ray image acquisition device of claim 22, wherein said X-ray detector comprises, as said one of said at least two distinct parts, a first subgroup of pixels and, as said different one of said at least two distinct parts, a second subgroup of pixels that is non-overlapping with said first subgroup of pixels.

24. The X-ray image acquisition device of claim 12, wherein said diffraction grating has an area comprising said first sub-area and said second sub-area, ones from among said portions of collectively said first sub-area and said second sub-area being arranged across said area in a chessboard pattern, from a standpoint of portion-wise belonging to said first sub-area versus portion-wise belonging to said second sub-area.

25. A diffraction grating configured for X-ray differential phase-contrast imaging having an X-ray-receiving face, said diffraction grating comprising:
multiple grating regions each having a plurality of bars, and a plurality of gaps that: a) alternate with the plurality of bars so as to space the plurality of bars apart such that the pitch is constant; and b) are transparent to X-rays,
such that said plurality of bars of a grating region from among said multiple grating regions change at least one of phase and amplitude of X-ray radiation incident upon said grating region via said X-ray receiving face, a change that would be evident by comparing said at least one of phase and amplitude correspondingly to at least one of phase and amplitude of said X-ray radiation that has passed through said grating region; and
multiple apertures, in said diffraction grating configured for X-ray differential phase-contrast imaging, that are regions transparent to X-rays;
wherein, laterally across said X-ray-receiving face, ones from among said multiple grating regions are disposed side-by-side with ones from among said multiple apertures, such that said ones from among said multiple grating regions are, in two mutually transverse lateral directions, arranged so as to alternate with said ones from among said multiple apertures in a chess-board pattern.

26. The diffraction grating of claim 25, said ones from among said multiple grating regions being flush with and thereby defining said X-ray-receiving face.

27. The diffraction grating of claim 25,
wherein: a) said multiple grating regions are arranged adjacent as correspondingly first subsets and/or second subsets; b) said multiple apertures are arranged adjacent as correspondingly first subsets and/or second subsets multiple apertures; or c) both a) and b); and
wherein correspondingly said first subsets and/or said second subsets are arranged, in respectively at least one direction, across said X-ray-receiving face in direction-wise correspondingly a first subset-repetition pitch $P_{SR1}$ and/or a second subset-repetition pitch $P_{SR2}$.

28. A detector arrangement of an X-ray system, said detector arrangement comprising:
an X-ray detector;
a phase grating; and
an analyzer grating, wherein each of said phase grating and said analyzer grating is configured as the diffraction grating of claim 25.

* * * * *